United States Patent
Raday et al.

(10) Patent No.: US 10,806,867 B2
(45) Date of Patent: Oct. 20, 2020

(54) INJECTOR

(71) Applicant: E3D AGRICULTURAL COOPERATIVE ASSOCIATION LTD., Kibbutz Bar-Am (IL)

(72) Inventors: Lior Raday, D.N. Ashkelon (IL); Ehud Carmel, Ganey Tikva (IL); Lior Mareli, Rehovot (IL); David Daily, Herzelia (IL); Guy Keenan, Tel Aviv (IL)

(73) Assignee: E3D AGRICULTURAL COOPERATIVE ASSOCIATION LTD., Bar Am (IL)

( * ) Notice: Subject to any disclaimer, the term of this patent is extended or adjusted under 35 U.S.C. 154(b) by 550 days.

(21) Appl. No.: 14/674,173

(22) Filed: Mar. 31, 2015

(65) Prior Publication Data

US 2015/0202379 A1 Jul. 23, 2015

Related U.S. Application Data

(63) Continuation of application No. 13/357,201, filed on Jan. 24, 2012, now Pat. No. 8,992,477.
(Continued)

(51) Int. Cl.
*A61M 5/32* (2006.01)
*A61M 5/20* (2006.01)
*A61M 5/24* (2006.01)

(52) U.S. Cl.
CPC ........ *A61M 5/3204* (2013.01); *A61M 5/2033* (2013.01); *A61M 2005/206* (2013.01);
(Continued)

(58) Field of Classification Search
CPC . A61M 5/3202; A61M 5/3204; A61F 5/0123; A61F 5/0106; A61F 2005/0167;
(Continued)

(56) References Cited

U.S. PATENT DOCUMENTS

| 2,398,544 A | 4/1946 | Lockhart |
| 2,459,875 A | 1/1949 | Folkman |

(Continued)

FOREIGN PATENT DOCUMENTS

| CA | 2356614 | 4/2000 |
| DE | 2019296 | 11/1971 |

(Continued)

OTHER PUBLICATIONS

US 5,954,699 A, 09/1999, Jost et al. (withdrawn)
(Continued)

*Primary Examiner* — Scott J Medway
(74) *Attorney, Agent, or Firm* — Sughrue Mion, PLLC

(57) ABSTRACT

An injector including a syringe arranged along a longitudinal axis, a removable cover for removable engagement with the syringe and a cover removal assembly including an outer portion which is engagable by a user and is movable axially in a cover disengagement direction along an axial travel path with respect to the longitudinal axis and an inner portion which includes at least one engagement portion which is engagable with the removable cover, whereby axial movement of the inner portion in the cover disengagement direction removes the removable cover from the syringe, at least one of the outer portion and the inner portion being configured such as to provide an axially floating lost motion engagement between the outer portion and the inner portion.

9 Claims, 12 Drawing Sheets

Related U.S. Application Data

(60) Provisional application No. 61/435,467, filed on Jan. 24, 2011, provisional application No. 61/472,232, filed on Apr. 6, 2011.

(52) U.S. Cl.
CPC ............... *A61M 2005/208* (2013.01); *A61M 2005/2418* (2013.01)

(58) Field of Classification Search
CPC . A61F 5/0109; A61F 2/38; A61F 5/01; A63B 71/1225; A41D 13/0568; A41D 13/0562
USPC ....... 604/198, 192, 232, 195, 196, 197, 223, 604/134–136, 157, 187
See application file for complete search history.

(56) References Cited

U.S. PATENT DOCUMENTS

| | | |
|---|---|---|
| 2,565,081 A | 8/1951 | Maynes |
| 2,591,457 A | 4/1952 | Maynes |
| 2,701,566 A | 2/1955 | Krug |
| 2,752,918 A | 7/1956 | Uytenbogaart |
| 2,832,339 A | 4/1958 | Sarnoff et al. |
| 2,888,924 A | 6/1959 | Dunmire |
| 2,960,087 A | 11/1960 | Uytenbogaart |
| 3,066,670 A | 4/1962 | Stauffer |
| 3,051,173 A | 8/1962 | Johnson et al. |
| 3,055,362 A | 9/1962 | Uytenbogaart |
| 3,136,313 A | 6/1964 | Enstrom et al. |
| 3,314,428 A | 4/1967 | Johnson et al. |
| 3,330,279 A | 7/1967 | Sarnoff et al. |
| 3,403,680 A | 10/1968 | Sinclair et al. |
| 3,543,603 A | 1/1970 | Gley |
| 3,605,743 A | 9/1971 | Arce |
| 3,618,603 A | 9/1971 | Levenson |
| 3,702,609 A | 11/1972 | Steiner |
| 3,712,301 A | 1/1973 | Sarnoff |
| 3,742,948 A | 7/1973 | Post |
| 3,797,488 A | 3/1974 | Hurschman et al. |
| 3,797,489 A | 3/1974 | Sarnoff |
| 3,880,163 A | 4/1975 | Ritterskamp |
| 3,882,863 A | 5/1975 | Sarnoff et al. |
| 3,892,237 A | 7/1975 | Steiner |
| 3,910,260 A | 10/1975 | Sarnoff et al. |
| 3,941,130 A | 3/1976 | Tibbs |
| 4,004,577 A | 1/1977 | Sarnoff |
| 4,031,893 A | 6/1977 | Kaplan et al. |
| 4,106,770 A | 8/1978 | Gray |
| 4,178,928 A | 12/1979 | Tischlinqer |
| 4,202,314 A | 5/1980 | Smirnov et al. |
| 4,214,584 A | 7/1980 | Smirnov et al. |
| 4,226,235 A | 10/1980 | Sarnoff et al. |
| 4,258,713 A | 3/1981 | Wardlow |
| 4,261,358 A | 4/1981 | Varqas et al. |
| 4,275,729 A | 6/1981 | Silver et al. |
| 4,333,457 A | 6/1982 | Margulies |
| 4,334,536 A * | 6/1982 | Pfleger ................... A61M 5/288 604/193 |
| 4,394,863 A | 7/1983 | Bartner |
| 4,425,120 A | 1/1984 | Sampson et al. |
| 4,437,859 A | 3/1984 | Whitehouse et al. |
| 4,447,231 A | 5/1984 | Bekkering |
| 4,530,695 A | 7/1985 | Phillips et al. |
| 4,565,543 A | 1/1986 | Bekkering et al. |
| 4,573,976 A | 3/1986 | Sampson et al. |
| 4,578,064 A | 3/1986 | Sarnoff et al. |
| 4,592,742 A | 6/1986 | Landau |
| 4,623,332 A | 11/1986 | Lindmayer et al. |
| 4,624,660 A | 11/1986 | Mijers et al. |
| 4,636,201 A * | 1/1987 | Ambrose ............... A61M 5/3202 604/192 |
| 4,637,403 A | 1/1987 | Garcia et al. |
| 4,664,653 A | 5/1987 | Saqstetter et al. |
| 4,678,461 A | 7/1987 | Mesa |
| 4,689,042 A | 8/1987 | Sarnoff et al. |
| 5,843,036 A | 1/1988 | Olive et al. |
| 4,723,937 A | 2/1988 | Sarnoff et al. |
| 4,742,910 A * | 5/1988 | Staebler .............. A61M 5/3213 206/365 |
| 4,755,169 A | 7/1988 | Sarnoff et al. |
| 4,787,891 A | 11/1988 | Levin |
| 4,795,432 A | 1/1989 | Karczmer |
| 4,795,433 A | 1/1989 | Sarnoff |
| 4,820,286 A | 4/1989 | van der Wal |
| 4,822,340 A | 4/1989 | Kamstra |
| 4,850,994 A | 7/1989 | Zerbs et al. |
| 4,852,768 A | 8/1989 | Bartsch |
| 4,902,279 A | 2/1990 | Schmidtz et al. |
| 4,923,447 A | 5/1990 | MorQan |
| 4,927,416 A | 5/1990 | Tomkiel |
| 4,929,237 A | 5/1990 | Medway |
| 4,955,868 A | 9/1990 | Klein |
| 4,964,866 A * | 10/1990 | Szwarc ............... A61M 5/3202 604/192 |
| 4,966,592 A | 10/1990 | Burns et al. |
| 4,986,817 A * | 1/1991 | Code .................. A61M 5/3213 604/192 |
| 4,994,034 A | 2/1991 | Botich et al. |
| 4,998,918 A | 3/1991 | Nimura |
| 5,041,088 A | 8/1991 | Ritson et al. |
| 5,042,977 A | 8/1991 | Bechtold et al. |
| 5,049,133 A | 9/1991 | Vilien Pascual |
| D322,479 S | 12/1991 | Miyaguchi |
| 5,085,641 A | 2/1992 | Sarnoff et al. |
| 5,092,842 A | 3/1992 | Bechtold et al. |
| 5,092,843 A | 3/1992 | Monroe et al. |
| 5,102,393 A | 4/1992 | Sarnoff et al. |
| 5,104,380 A | 4/1992 | Holman et al. |
| 5,114,406 A | 5/1992 | Gabriel et al. |
| 5,114,410 A | 5/1992 | Caralt Battle |
| 5,137,516 A | 8/1992 | Rand et al. |
| 5,141,496 A | 8/1992 | Dalto |
| 5,163,918 A | 11/1992 | Righi |
| 5,201,708 A | 4/1993 | Martin |
| 5,215,536 A | 6/1993 | Lampropoulos et al. |
| 5,224,936 A | 7/1993 | GaliaQher |
| 5,242,240 A | 9/1993 | Gorham |
| 5,244,465 A | 9/1993 | Michel |
| 5,259,840 A | 9/1993 | Boris |
| 5,263,934 A | 11/1993 | Haak |
| 5,267,963 A | 12/1993 | Bachynsky |
| 5,267,976 A | 12/1993 | Guerineau et al. |
| 5,273,544 A | 12/1993 | van der Wal |
| D343,897 S | 2/1994 | Rand et al. |
| 5,282,793 A | 2/1994 | Larson |
| 5,295,965 A | 3/1994 | Wimot |
| 5,295,975 A | 3/1994 | Lockwood |
| 5,298,024 A | 3/1994 | Richmond |
| D346,219 S | 4/1994 | Fardigh |
| 5,300,030 A | 4/1994 | Crossman |
| 5,318,538 A | 6/1994 | Martin |
| 5,320,609 A | 6/1994 | Haber et al. |
| 5,334,144 A | 8/1994 | Alchas et al. |
| 5,342,308 A | 8/1994 | Boschetti |
| 5,346,480 A | 9/1994 | Hess |
| 5,358,489 A | 10/1994 | Wyrick |
| 5,376,080 A | 12/1994 | Petrussa |
| 5,378,233 A | 1/1995 | Haber et al. |
| 5,383,865 A | 1/1995 | Michel |
| 5,391,151 A | 2/1995 | Wilmot |
| 5,425,715 A | 6/1995 | Daliing et al. |
| 5,433,712 A | 7/1995 | Stiles |
| 5,478,316 A * | 12/1995 | Bitdinger ............ A61M 5/2033 604/134 |
| 5,480,387 A | 1/1996 | Gabriel et al. |
| 5,527,287 A | 6/1996 | Miskinyar |
| 5,531,705 A | 7/1996 | Alter et al. |
| 5,565,553 A | 10/1996 | Deitz et al. |
| 5,569,192 A | 10/1996 | van der Wal |
| 5,584,815 A | 12/1996 | Pawelka et al. |
| 5,591,138 A | 1/1997 | Vaillancourt |
| 5,599,309 A * | 2/1997 | Marshall ............ A61M 5/2033 604/117 |

(56) References Cited

U.S. PATENT DOCUMENTS

| | | |
|---|---|---|
| 5,616,128 A | 4/1997 | Meyer |
| 5,620,421 A | 4/1997 | Schmitz |
| 5,634,906 A | 6/1997 | Haber |
| 5,637,094 A | 6/1997 | Stewart, Jr. et al. |
| 5,645,534 A | 7/1997 | Chanoch |
| 5,658,259 A | 8/1997 | Pearson et al. |
| 5,665,071 A | 9/1997 | Wyrick |
| 5,681,291 A | 10/1997 | Galli |
| 5,695,472 A | 12/1997 | Wyrick |
| 5,709,662 A | 1/1998 | Olive et al. |
| 5,744,360 A | 4/1998 | Hu et al. |
| 5,779,677 A | 7/1998 | Frezza |
| 5,807,335 A | 9/1998 | Kriesel et al. |
| 5,817,111 A | 10/1998 | Riza |
| 5,823,998 A | 10/1998 | Yamagata |
| 5,851,197 A | 12/1998 | Marano |
| 5,885,250 A | 3/1999 | Kriesel et al. |
| 5,928,205 A | 7/1999 | Marshall |
| 5,931,817 A | 8/1999 | Nguyen et al. |
| 5,957,886 A | 9/1999 | Weston |
| 5,957,897 A | 9/1999 | Jeffrey |
| 5,980,491 A | 11/1999 | Hansen |
| 5,984,900 A | 11/1999 | Mikkelsen |
| 5,993,421 A | 11/1999 | Kriesel |
| 6,015,396 A | 1/2000 | Buttgen et al. |
| 6,048,336 A | 4/2000 | Gabriel |
| 6,056,728 A | 5/2000 | von Schuckmann |
| 6,070,623 A | 6/2000 | Aneas |
| 6,077,247 A | 6/2000 | Marshall et al. |
| 6,090,070 A | 7/2000 | Hager et al. |
| 6,090,080 A | 7/2000 | Jost et al. |
| 6,090,382 A | 7/2000 | Salfeld et al. |
| 6,099,503 A | 8/2000 | Stradella |
| 6,099,504 A | 8/2000 | Gross et al. |
| 6,102,896 A | 8/2000 | Roser |
| 6,110,147 A | 8/2000 | Perouse |
| 6,149,626 A | 11/2000 | Bachynsky et al. |
| 6,159,181 A | 12/2000 | Crossman et al. |
| 6,171,285 B1 | 1/2001 | Johnson |
| 6,203,530 B1 | 3/2001 | Stewart, Sr. |
| 6,210,369 B1 | 4/2001 | Wilmot et al. |
| 6,213,987 B1 | 4/2001 | Hirsch |
| 6,221,044 B1 | 4/2001 | Greco |
| 6,241,708 B1 | 6/2001 | Reilly et al. |
| 6,241,709 B1 | 6/2001 | Bechtold et al. |
| 6,258,068 B1 | 7/2001 | Kirchofer et al. |
| 6,258,562 B1 | 7/2001 | Salfeld |
| 6,270,479 B1 | 8/2001 | Bergens et al. |
| 6,277,097 B1 | 8/2001 | Mikkelsen et al. |
| 6,277,098 B1 | 8/2001 | Klitmose et al. |
| 6,277,099 B1 | 8/2001 | Strowe et al. |
| 6,280,421 B1 | 8/2001 | Kirchofer et al. |
| 6,312,412 B1 | 11/2001 | Saied et al. |
| 6,319,233 B1 | 11/2001 | Jansen |
| 6,319,234 B1 | 11/2001 | Resfelli et al. |
| 6,322,540 B1 | 11/2001 | Grabis |
| 6,371,939 B2 | 4/2002 | Bergens |
| 6,387,074 B1 | 5/2002 | Horppu et al. |
| 6,387,078 B1 | 5/2002 | Gillespie, III |
| 6,413,237 B1 | 7/2002 | Caizza et al. |
| 6,419,658 B1 | 7/2002 | Resfelli et al. |
| D461,555 S | 8/2002 | Binet |
| 6,475,194 B2 | 11/2002 | Oomici |
| 6,509,015 B1 | 1/2003 | Salfeld |
| 6,517,517 B1 | 2/2003 | Farrugia et al. |
| 6,656,163 B1 | 2/2003 | Marshall et al. |
| 6,656,164 B1 | 2/2003 | Smith |
| 6,530,903 B2 | 3/2003 | Wang et al. |
| 6,544,234 B1 * | 4/2003 | Gabriel ............... A61M 5/2033 604/134 |
| 6,572,590 B1 | 6/2003 | Stevens et al. |
| 6,575,939 B1 | 6/2003 | Brunei |
| 6,585,690 B1 | 7/2003 | Hoeck |
| 6,589,210 B1 | 7/2003 | Rolfe |
| 6,592,555 B1 | 7/2003 | Wen-Pi |
| 6,595,962 B1 | 7/2003 | Perthu |
| 6,605,058 B1 | 8/2003 | Wich |
| 6,605,067 B1 | 8/2003 | Larsen |
| 6,607,508 B2 | 8/2003 | Knau |
| 6,613,019 B2 | 9/2003 | Munk |
| 6,620,137 B2 | 9/2003 | Kirchhofer et al. |
| 6,638,255 B1 | 10/2003 | Weber |
| 6,673,035 B1 | 1/2004 | Rice et al. |
| 6,673,049 B2 | 1/2004 | Hommann |
| 6,685,676 B2 | 2/2004 | Jansen et al. |
| 6,692,469 B1 | 2/2004 | Weekes et al. |
| 6,712,788 B2 | 3/2004 | Righi |
| 6,743,203 B1 | 6/2004 | Pickhard |
| 6,752,798 B2 | 6/2004 | McWethy |
| 6,767,336 B1 | 7/2004 | Kaplan |
| D494,270 S | 8/2004 | Reschke |
| 6,773,415 B2 | 8/2004 | Heiniger |
| 6,796,967 B2 | 9/2004 | Jensen |
| 6,802,827 B2 | 10/2004 | Andersson |
| 6,805,686 B1 | 10/2004 | Fathallah et al. |
| 6,808,507 B2 | 10/2004 | Roser |
| 6,817,989 B2 | 11/2004 | Svendsen |
| 6,872,194 B2 | 3/2005 | Ooyle et al. |
| 6,926,697 B2 | 8/2005 | Malenchek |
| 6,932,793 B1 | 8/2005 | Marshall et al. |
| 6,945,960 B2 | 9/2005 | Barker |
| 6,971,999 B2 | 12/2005 | Py et al. |
| 6,976,976 B2 | 12/2005 | Ooyle |
| 6,986,760 B2 | 1/2006 | Giambattista |
| 7,001,364 B1 | 2/2006 | Farhi |
| 7,004,929 B2 | 2/2006 | McWethy |
| D518,175 S | 3/2006 | Hammann et al. |
| 7,056,306 B1 | 6/2006 | Halseth |
| 7,097,634 B2 | 8/2006 | Gilbert |
| 7,128,728 B2 | 10/2006 | Kirchhofer |
| 7,223,394 B2 | 5/2007 | Salfeld |
| 7,300,420 B2 | 11/2007 | Doyle |
| 7,320,682 B2 | 1/2008 | Cocker |
| 7,357,790 B2 | 4/2008 | Hommann |
| 7,357,791 B2 | 4/2008 | Kirchhofer |
| 7,361,160 B2 | 4/2008 | Hommann et al. |
| 7,442,185 B2 | 10/2008 | Amark |
| 7,442,186 B2 | 10/2008 | Blomquist |
| 7,476,217 B2 | 1/2009 | Martin |
| 7,497,847 B2 | 3/2009 | Crawford et al. |
| 7,541,031 B2 | 6/2009 | Salfeld |
| 7,569,035 B1 | 8/2009 | Wilmot |
| 7,588,761 B2 | 9/2009 | Salfeld |
| 7,597,685 B2 | 10/2009 | Olson |
| 7,694,828 B2 | 4/2010 | Swift et al. |
| 7,717,877 B2 | 5/2010 | Lavi |
| 7,736,333 B2 | 6/2010 | Gillespie, III |
| D622,374 S | 8/2010 | Crawford |
| 7,771,397 B1 | 8/2010 | Olson |
| D629,509 S | 12/2010 | Swift et al. |
| 7,863,426 B2 | 1/2011 | Wan et al. |
| 7,905,866 B2 * | 3/2011 | Haider ............... A61M 5/2033 604/137 |
| 7,919,264 B2 | 4/2011 | Maksymowych |
| 7,931,625 B2 | 4/2011 | Kirchhofer |
| 7,931,626 B2 | 4/2011 | Kirchhofer |
| 7,938,802 B2 | 5/2011 | Bicknell |
| 7,976,499 B2 | 7/2011 | Grunhut |
| 8,048,035 B2 | 11/2011 | Mesa et al. |
| 8,162,887 B2 | 4/2012 | Bicknell |
| 8,597,255 B2 | 12/2013 | Emmott et al. |
| 8,827,961 B2 | 9/2014 | Emmott et al. |
| 2001/0005781 A1 | 6/2001 | Bergens |
| 2001/0021821 A1 | 9/2001 | Wang |
| 2001/0037087 A1 | 11/2001 | Knauer |
| 2001/0044606 A1 | 11/2001 | Inkpen |
| 2001/0053896 A1 | 12/2001 | Caizza |
| 2001/0053894 A1 | 12/2001 | Jensen |
| 2002/0002344 A1 | 1/2002 | Douqlas |
| 2002/0016563 A1 | 2/2002 | Hill |
| 2002/0042592 A1 | 4/2002 | Wilmot |
| 2002/0095120 A1 | 7/2002 | Larsen |
| 2002/0111587 A1 | 8/2002 | Hommann |
| 2002/0133122 A1 | 10/2002 | Shaw |

(56) References Cited

U.S. PATENT DOCUMENTS

| | | |
|---|---|---|
| 2002/0161337 A1 | 10/2002 | Shaw |
| 2002/0169408 A1 | 11/2002 | Beretta |
| 2002/0183690 A1 | 12/2002 | Arnisolle |
| 2003/0004466 A1 | 1/2003 | Bitdinger |
| 2003/0004467 A1 | 1/2003 | Musick |
| 2003/0023203 A1 | 1/2003 | Lavi |
| 2003/0023205 A1 | 1/2003 | Botich |
| 2003/0050606 A1 | 3/2003 | Brand |
| 2003/0093036 A1 | 5/2003 | Crossman |
| 2003/0105430 A1 | 6/2003 | Lavi |
| 2003/0187401 A1 | 10/2003 | Doyle |
| 2003/0212362 A1 | 11/2003 | Roser |
| 2003/0229308 A1 | 12/2003 | Tsals |
| 2003/0236502 A1 | 12/2003 | De La Serna et al. |
| 2004/0019326 A1 | 1/2004 | Gilbert et al. |
| 2004/0024367 A1 | 2/2004 | Gilbert |
| 2004/0039336 A1 | 2/2004 | Amark |
| 2004/0039337 A1 | 2/2004 | Letzinq |
| 2004/0054327 A1 | 3/2004 | Gillespie |
| 2004/0147875 A1 | 7/2004 | Wallace |
| 2004/0199117 A1 | 10/2004 | Giambattista |
| 2004/0215151 A1 | 10/2004 | Marshall |
| 2004/0225262 A1 | 11/2004 | Fathallah |
| 2005/0020979 A1 | 1/2005 | Westbye et al. |
| 2005/0020984 A1 | 1/2005 | Lesch |
| 2005/0027255 A1 | 2/2005 | Lavi |
| 2005/0049550 A1 | 3/2005 | Kirchofer |
| 2005/0049561 A1 | 3/2005 | Hommann |
| 2005/0075611 A1* | 4/2005 | Hetzler ............... A61L 2/0011 604/192 |
| 2005/0085776 A1 | 4/2005 | Hommann et al. |
| 2005/0096597 A1 | 5/2005 | Crawford |
| 2005/0101919 A1 | 5/2005 | Brunnberq |
| 2005/0124940 A1 | 6/2005 | Martin et al. |
| 2005/0137534 A1 | 6/2005 | Hommann |
| 2005/0137571 A1 | 6/2005 | Hommann |
| 2005/0165360 A1 | 7/2005 | Stamp |
| 2005/0165361 A1 | 7/2005 | Marshall et al. |
| 2005/0165362 A1 | 7/2005 | Slawson |
| 2005/0165363 A1 | 7/2005 | Judson et al. |
| 2005/0171476 A1 | 8/2005 | Judson et al. |
| 2005/0171477 A1 | 8/2005 | Rubin et al. |
| 2005/0273054 A1 | 8/2005 | Asch |
| 2005/0209569 A1 | 9/2005 | Ishikawa et al. |
| 2005/0222539 A1 | 10/2005 | Gonzales et al. |
| 2005/0222540 A1 | 10/2005 | Kirchofer et al. |
| 2005/0261634 A1 | 11/2005 | Karlsson |
| 2005/0273055 A1 | 12/2005 | Harrisson et al. |
| 2005/0273061 A1 | 12/2005 | Hommann et al. |
| 2005/0277885 A1 | 12/2005 | Scherer |
| 2005/0277886 A1 | 12/2005 | Hommann et al. |
| 2005/0277893 A1 | 12/2005 | Liversidge |
| 2005/0288633 A1 | 12/2005 | Jeffrey |
| 2006/0030819 A1 | 2/2006 | Young et al. |
| 2006/0036216 A1 | 2/2006 | Rimlinger et al. |
| 2006/0047250 A1 | 3/2006 | Hickinbotham et al. |
| 2006/0069350 A1 | 3/2006 | Buenger et al. |
| 2006/0069354 A1 | 3/2006 | Buenger et al. |
| 2006/0100588 A1 | 5/2006 | Brunnberg et al. |
| 2006/0111666 A1 | 5/2006 | Hommann et al. |
| 2006/0111674 A1 | 5/2006 | Vedrine |
| 2006/0129122 A1 | 6/2006 | Wyrick |
| 2006/0167413 A1 | 7/2006 | Marshall et al. |
| 2006/0189933 A1 | 8/2006 | Alheidt |
| 2006/0253083 A1 | 11/2006 | Liu |
| 2007/0049865 A1 | 3/2007 | Radmer et al. |
| 2007/0118081 A1 | 5/2007 | Liversidge |
| 2007/0129674 A1 | 6/2007 | Daily et al. |
| 2007/0129686 A1* | 6/2007 | Daily ............... A61M 5/2033 604/192 |
| 2007/0142776 A9 | 6/2007 | Daily |
| 2007/0156088 A1 | 7/2007 | Chen et al. |
| 2007/0161960 A1 | 7/2007 | Zinger |
| 2007/0173772 A1 | 7/2007 | Chelak |
| 2007/0239117 A1 | 10/2007 | Liversidge |
| 2008/0009789 A1 | 1/2008 | Judd |
| 2008/0097337 A1 | 4/2008 | Paproski |
| 2008/0208125 A1 | 8/2008 | Bicknell et al. |
| 2008/0208140 A1 | 8/2008 | Barrelle |
| 2008/0249477 A1 | 10/2008 | James |
| 2008/0269692 A1 | 10/2008 | Chandrasekaran |
| 2008/0300549 A1 | 12/2008 | Verespej |
| 2009/0024076 A1 | 1/2009 | Babaev |
| 2009/0024093 A1 | 1/2009 | Carrel |
| 2009/0036870 A1 | 2/2009 | Mounce et al. |
| 2009/0157012 A1 | 6/2009 | Magne |
| 2009/0182284 A1 | 7/2009 | Morgan |
| 2009/0204076 A1 | 8/2009 | Liversidge |
| 2009/0240210 A1 | 9/2009 | Walton |
| 2009/0299328 A1 | 12/2009 | Mudd et al. |
| 2010/0036318 A1 | 2/2010 | Liversidqe |
| 2010/0137810 A1 | 6/2010 | Raday |
| 2010/0160869 A1 | 6/2010 | Gillespie |
| 2010/0160894 A1 | 6/2010 | Julian |
| 2010/0185178 A1* | 7/2010 | Sharp ............... A61M 5/002 604/506 |
| 2011/0054414 A1 | 3/2011 | Shang |
| 2011/0098641 A1 | 4/2011 | Haider et al. |
| 2011/0178500 A1 | 7/2011 | Shang |
| 2012/0022499 A1 | 1/2012 | Anderson |
| 2012/0107783 A1 | 5/2012 | Julian |
| 2012/0172810 A1 | 7/2012 | Bicknell |
| 2012/0197209 A1 | 8/2012 | Hauri |
| 2012/0233834 A1 | 9/2012 | Szechinski |
| 2012/0289905 A1 | 11/2012 | Julian |
| 2013/0245553 A1 | 3/2013 | Mesa et al. |

FOREIGN PATENT DOCUMENTS

| | | |
|---|---|---|
| DE | 19821933 | 11/1999 |
| DE | 60207576 | 6/2006 |
| EP | 68864 | 1/1983 |
| EP | 1034809 | 9/2000 |
| EP | 1334740 | 8/2003 |
| EP | 666084 | 4/2004 |
| EP | 1364667 | 4/2005 |
| EP | 1349590 | 5/2006 |
| EP | 2085104 | 8/2009 |
| EP | 1654020 | 3/2010 |
| EP | 620748 | 7/2010 |
| EP | 1518575 | 11/2010 |
| EP | 1590023 | 5/2011 |
| EP | 2361648 | 8/2011 |
| EP | 1523360 | 9/2013 |
| FR | 2770404 | 5/1999 |
| GB | 2243552 | 11/1991 |
| GB | 2388033 | 11/2003 |
| GB | 2465389 | 5/2010 |
| JP | 50-14835 | 5/1975 |
| JP | 5-161712 | 6/1993 |
| JP | 2001-512038 | 8/2001 |
| JP | 2006507060 | 3/2006 |
| RU | 2004256 | 12/1993 |
| RU | 2131748 | 6/1999 |
| RU | 2169584 | 6/2001 |
| WO | 93/13819 | 7/1993 |
| WO | 94/09839 | 5/1994 |
| WO | 94/13342 | 6/1994 |
| WO | 94/26333 | 11/1994 |
| WO | 99/003529 | 1/1999 |
| WO | 99/22789 | 5/1999 |
| WO | 01/37908 | 5/2001 |
| WO | 01/62319 | 8/2001 |
| WO | 02/47746 | 6/2002 |
| WO | 03/011378 | 2/2003 |
| WO | 03/039633 | 5/2003 |
| WO | 03/047663 | 6/2003 |
| WO | 03/077968 | 9/2003 |
| WO | 03/097133 | 11/2003 |
| WO | 04/000397 | 12/2003 |
| WO | 03/099358 | 3/2004 |
| WO | 04/047892 | 6/2004 |
| WO | 04/060451 | 7/2004 |
| WO | 04/067068 | 8/2004 |

(56) References Cited

FOREIGN PATENT DOCUMENTS

| WO | 05/002653 | 1/2005 |
|---|---|---|
| WO | 05/025636 | 3/2005 |
| WO | 05/025637 | 3/2005 |
| WO | 2005/021070 | 3/2005 |
| WO | 05/046765 | 5/2005 |
| WO | 05/079889 | 9/2005 |
| WO | 05/086587 | 9/2005 |
| WO | 05/090836 | 9/2005 |
| WO | 05/0113039 | 12/2005 |
| WO | 05/115508 | 12/2005 |
| WO | 05/115509 | 12/2005 |
| WO | 05/115510 | 12/2005 |
| WO | 05/115511 | 12/2005 |
| WO | 05/115512 | 12/2005 |
| WO | 05/115513 | 12/2005 |
| WO | 05/115516 | 12/2005 |
| WO | 06/000785 | 1/2006 |
| WO | 06/058061 | 6/2006 |
| WO | 2006/063015 | 6/2006 |
| WO | 2006063015 | 6/2006 |
| WO | 04/060445 | 7/2007 |
| WO | 2008/029280 | 3/2008 |
| WO | 08/047372 | 4/2008 |
| WO | 08/005315 | 1/2009 |
| WO | 2009/040601 | 4/2009 |
| WO | 2009/040603 | 4/2009 |
| WO | 2009040603 | 4/2009 |
| WO | 2009/155277 | 12/2009 |
| WO | 2010136076 | 12/2010 |
| WO | 2012101629 | 8/2012 |

OTHER PUBLICATIONS

An Office Action dated Jun. 29, 2010, which issued during the prosecution of Applicant's U.S. Appl. No. 10/572,215.
A Supplementary European Search Report dated Feb. 12, 2010, which issued during the prosecution of Applicant's European Patent Application No. EP 04 77 0522.
A Supplementary European Search Report dated Mar. 4, 2010, which issued during the prosecution of Applicant's European Patent Application No. EP 04 77 0523.
J. Hamilton, "Needle Phobia: a Neglected Diagnosis". Journal of Family Practice, 1995: 41: 16-175.
An International Search Report dated Feb. 28, 2006, which issued during the prosecution of Applicant's PCT/IL04/00851.
An Office Action dated Feb. 10, 2012, which issued during the prosecution of European Patent Application No. 04770522.
A Hearing Notice in Reference prosecution of Indian Patent dated Jan. 19, 2012, which issued during the Application No. 426/MUMNP/2006.
An Office Action dated Jul. 7, 2011 which issued during the prosecution of Canadian Patent Application No. 2,539,315.
An Office Action dated Mar. 19, 2012, which issued during the prosecution of U.S. Appl. No. 12/741,628.
An Office Action dated Oct. 7, 2010, which issued during the prosecution of U.S. Appl. No. 12/446,168.
An Office Action dated May 26, 2011, which issued during the prosecution of U.S. Appl. No. 12/446,168.
An Office Action dated May 11, 2012, which issued during the prosecution of U.S. Appl. No. 12/446,168.
An Office Action dated Feb. 10, 2011, which issued during the prosecution of U.S. Appl. No. 10/572,214.
An International Search Report prosecution of Applicant's dated Feb. 24, 2006, which issued during the PCT/IL04/00852.
An Office Action dated Oct. 7, 2011, which issued during the prosecution of U.S. Appl. No. 10/572,214.
A Notice of Allowance dated of US Patent Application dated Jun. 8, 2012, which issued during the prosecution U.S. Appl. No. 10/572,214.
An International Search Report which issued during the prosecution and a Written Opinion both dated May 15, 2012, of Applicant's PCT/IL2012/000037.
U.S. Appl. No. 61/435,467, filed Jan. 24, 2011.
U.S. Appl. No. 61/472,232, filed Apr. 6, 2011.
An International Preliminary Report on Patentability dated Jul. 30, 2013, which issued during the prosecution of Applicant's PCT/IL2012/000037.
A Notice of Allowance dated Dec. 5, 2014, which issued during the prosecution of U.S. Appl. No. 13/357,201.
An Office Action dated Nov. 18, 2013, which issued during the prosecution of U.S. Appl. No. 13/357,201.
An Office Action dated Jul. 31, 2014, which issued during the prosecution of U.S. Appl. No. 13/357,201.

* cited by examiner

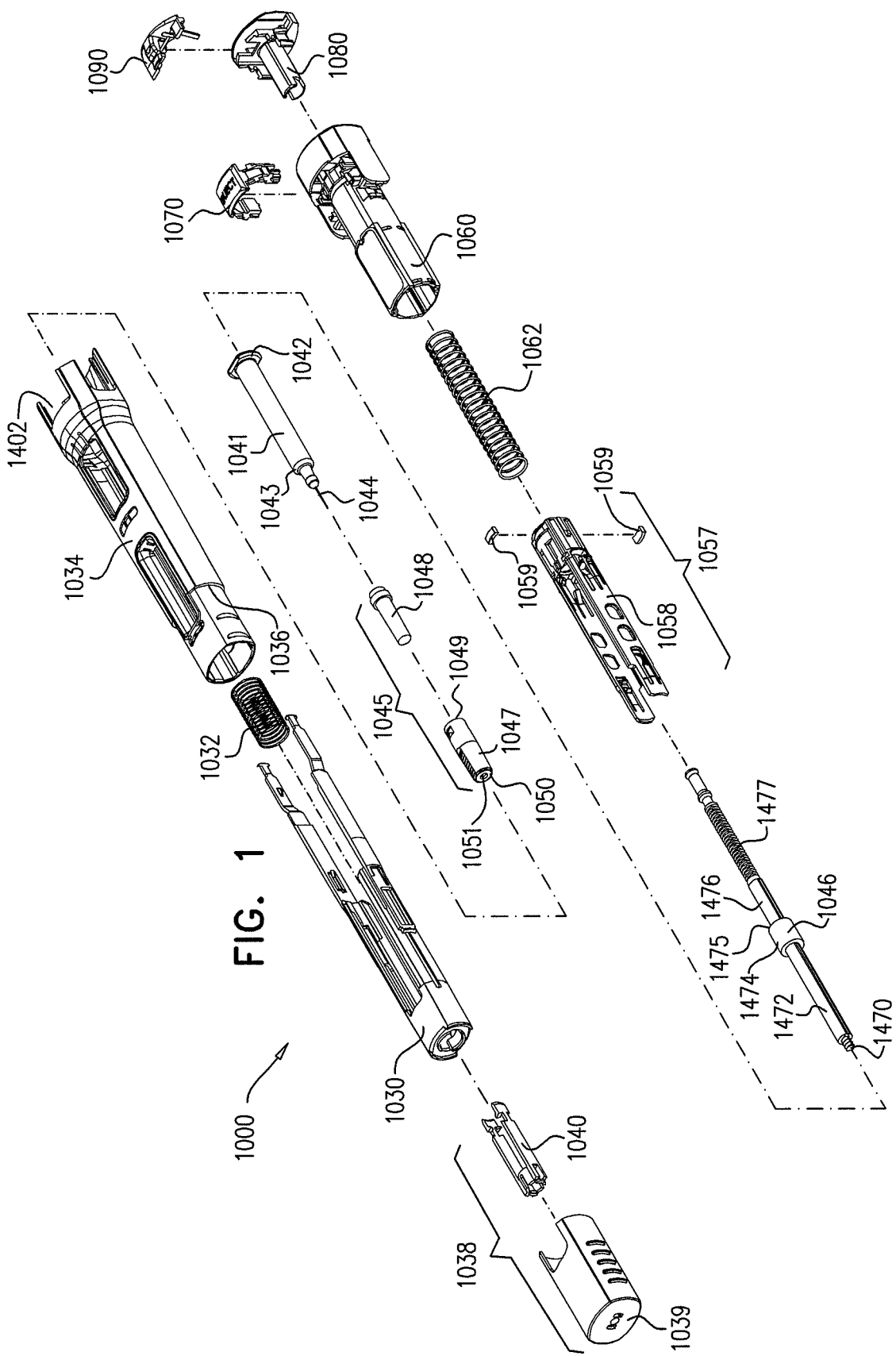

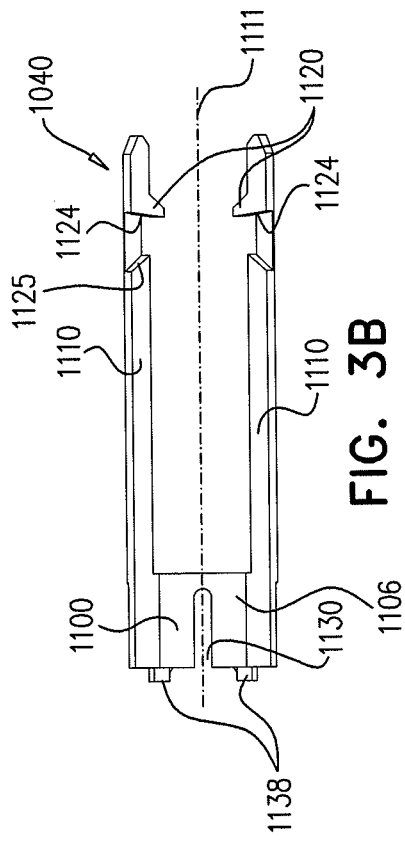
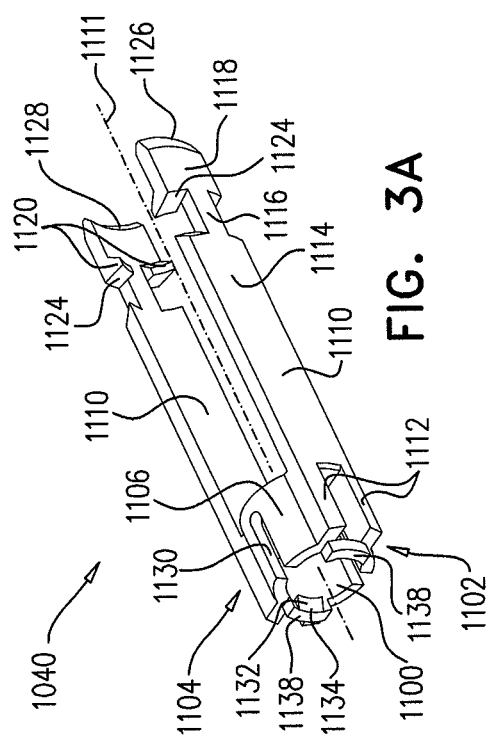
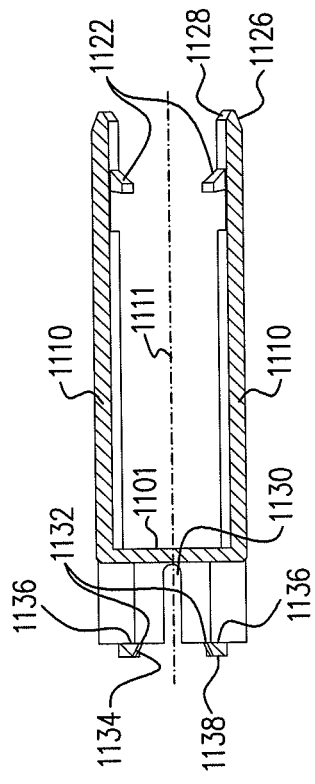
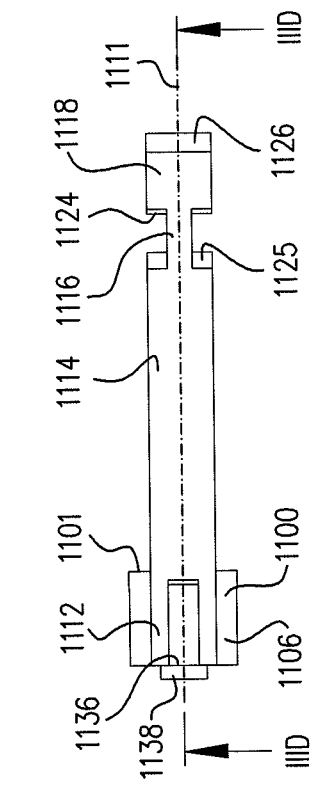

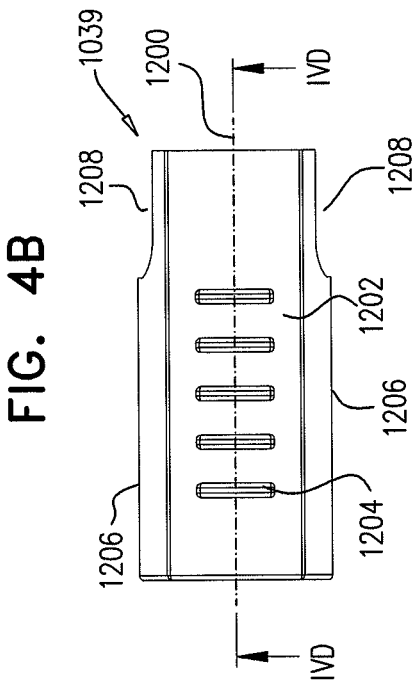
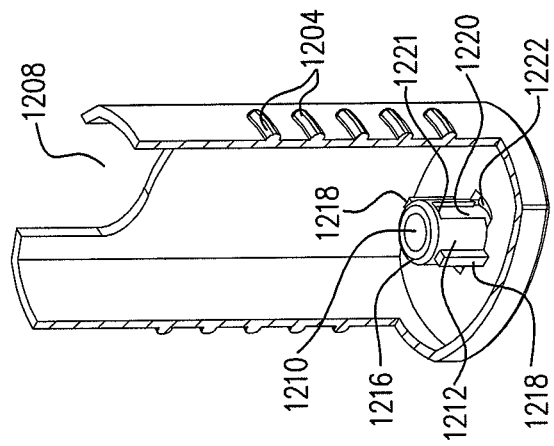
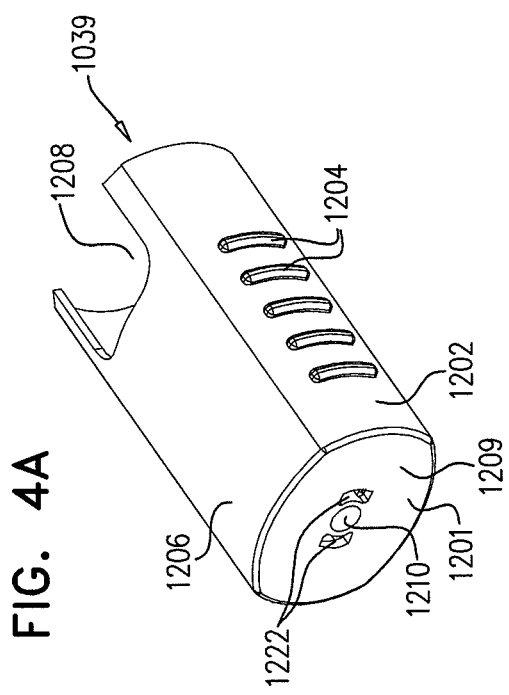
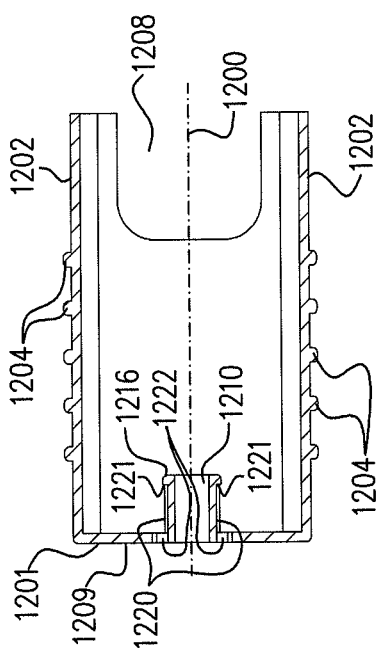

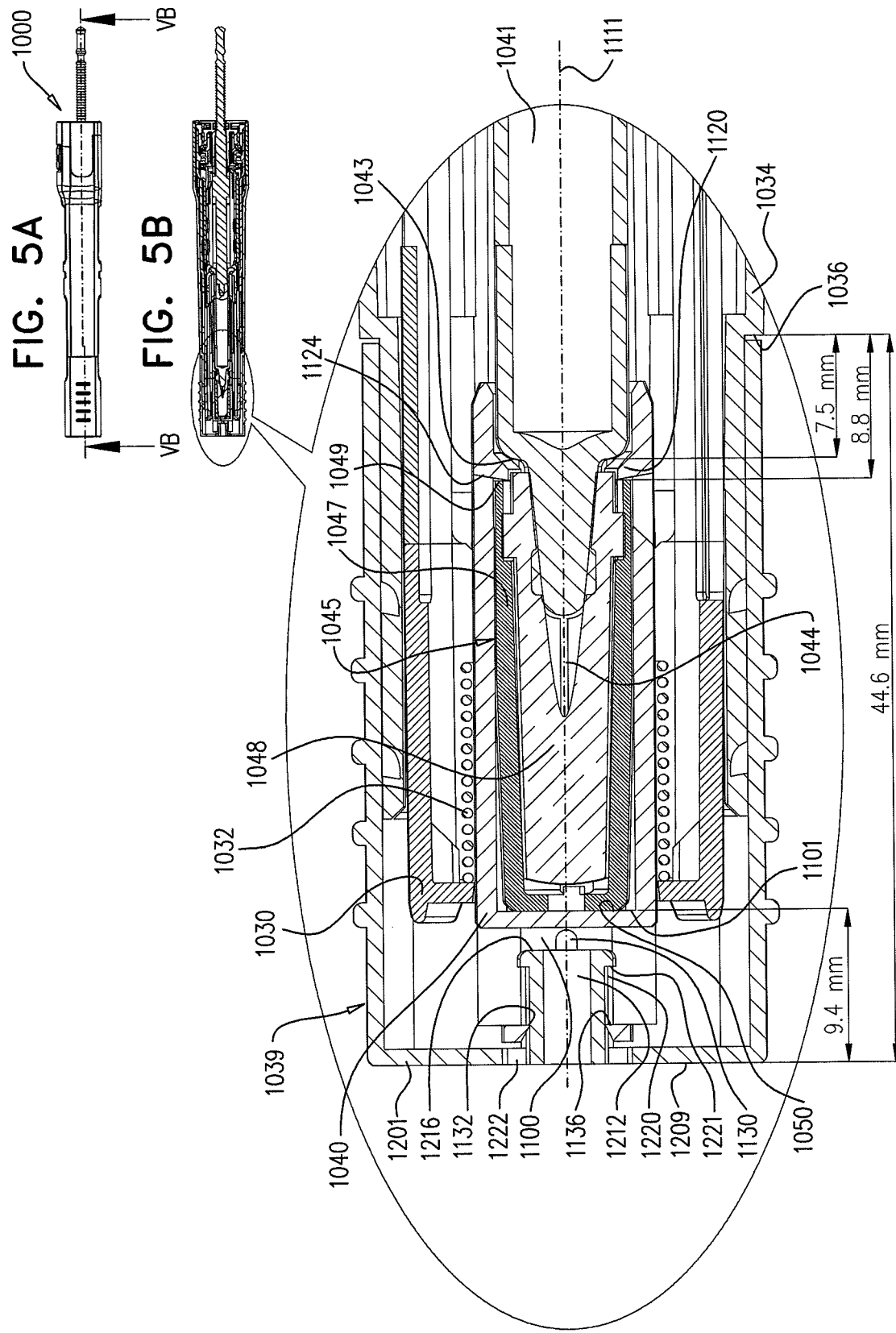

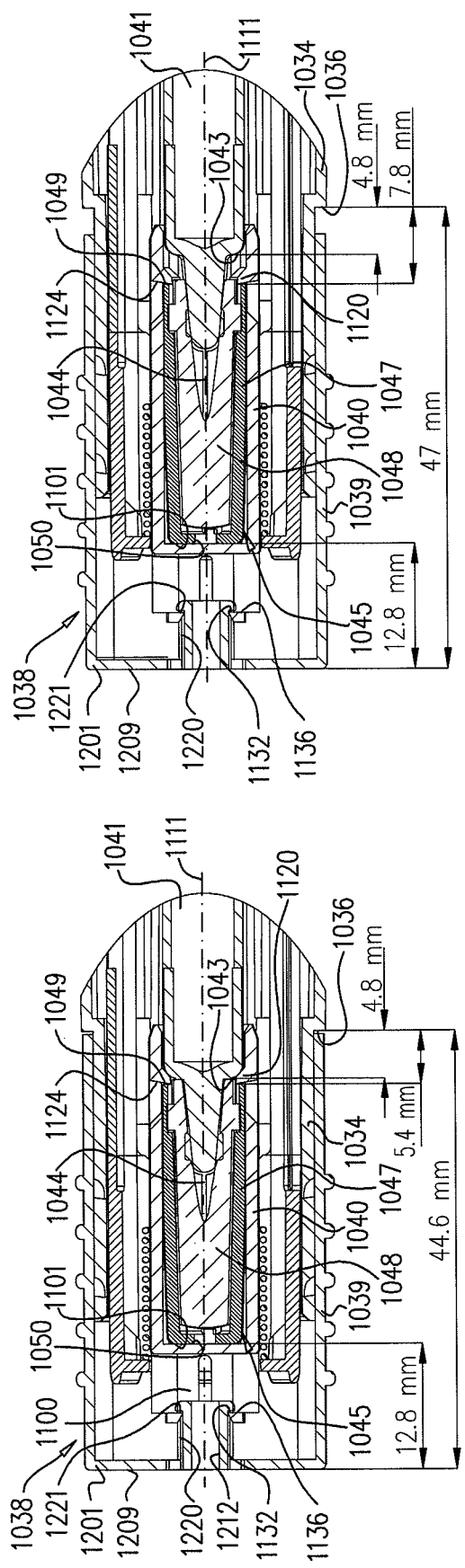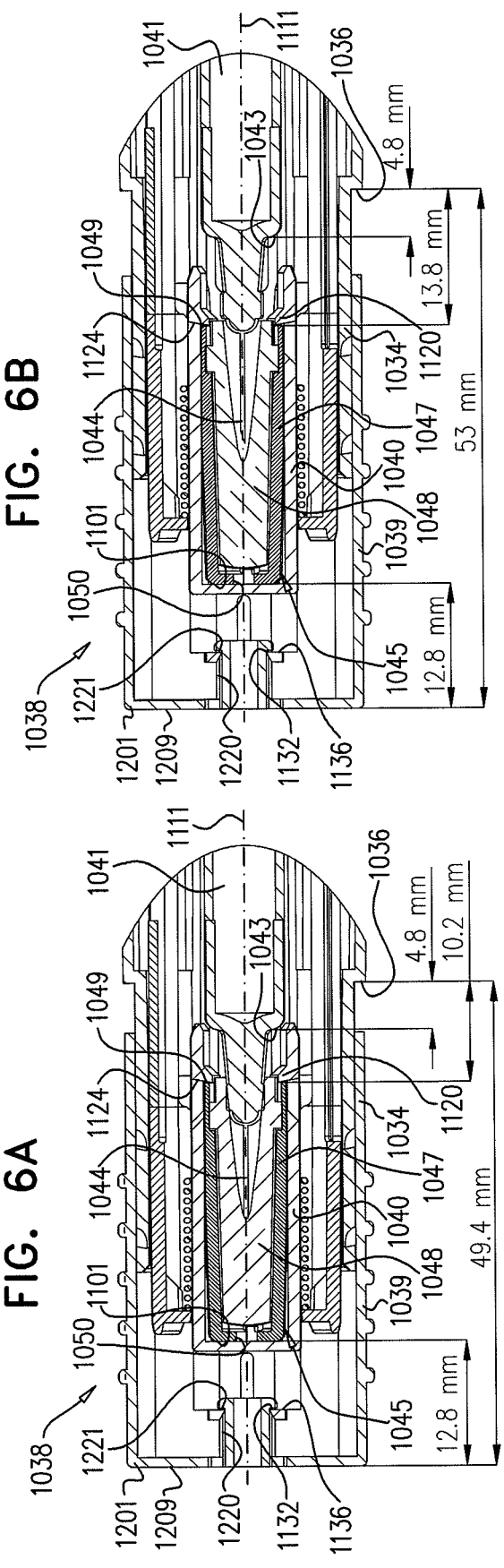

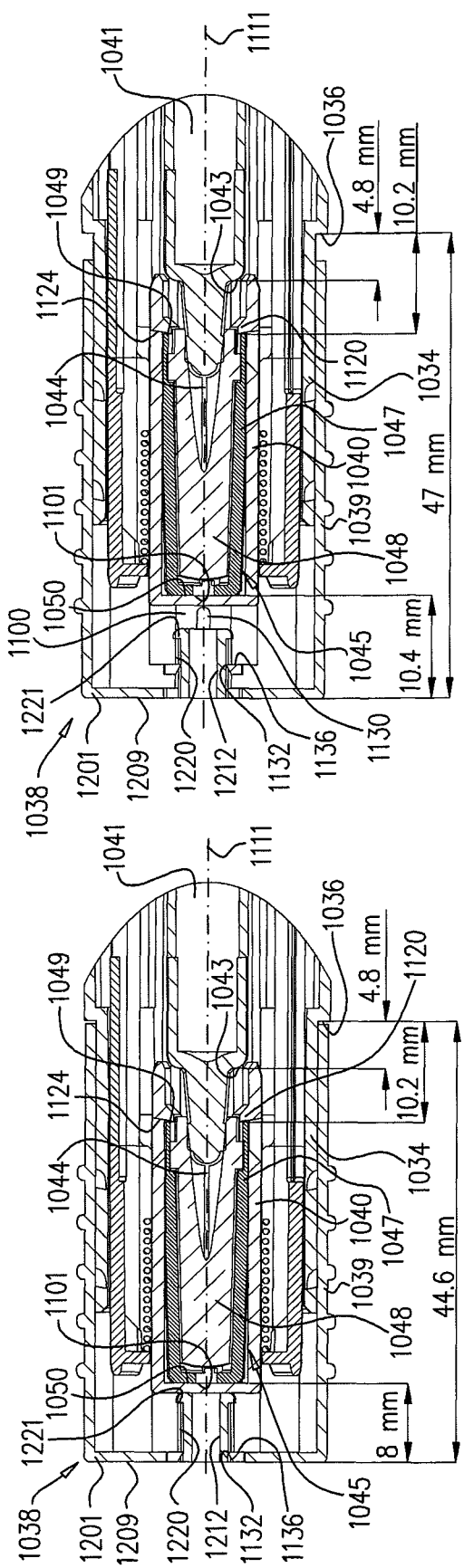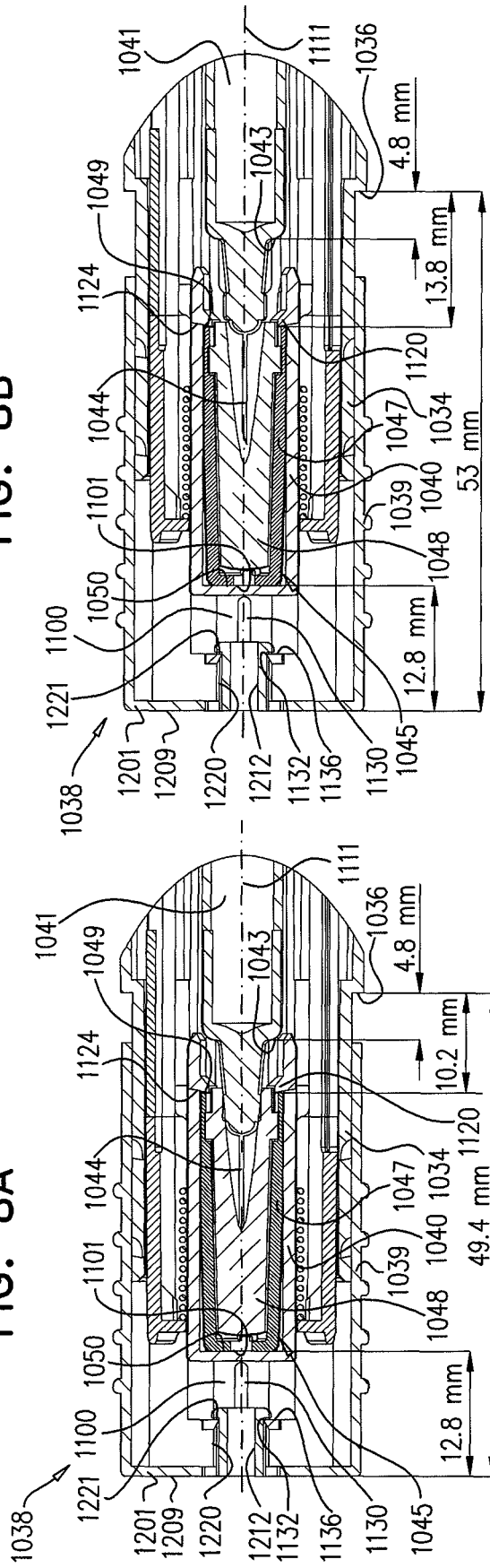
FIG. 8A  FIG. 8B  FIG. 8C  FIG. 8D

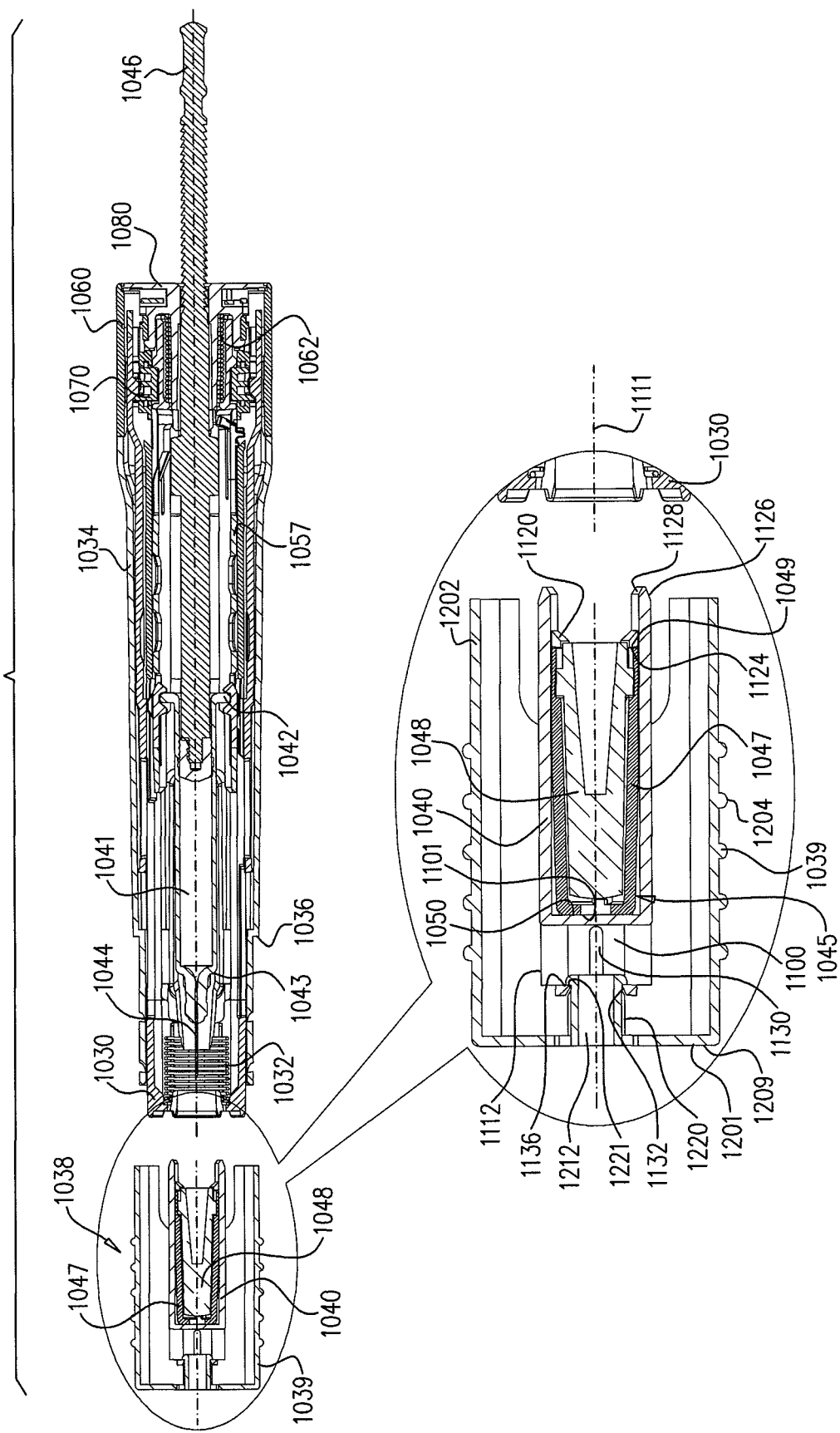

INJECTOR

REFERENCE TO RELATED APPLICATIONS

Reference is made to U.S. Provisional Patent Application Ser. No. 61/435,467 filed Jan. 24, 2011, the disclosure of which is hereby incorporated by reference and priority of which is hereby claimed pursuant to 37 CFR 1.78(a) (4) and (5)(i).

Reference is made to U.S. Provisional Patent Application Ser. No. 61/472,232, filed Apr. 6, 2011, the disclosure of which is hereby incorporated by reference and priority of which is hereby claimed pursuant to 37 CFR 1.78(a) (4) and (5)(i).

FIELD OF THE INVENTION

The present invention relates to injectors generally.

BACKGROUND OF THE INVENTION

The following patent publications are believed to represent the current state of the art:

U.S. Pat. No. 7,597,685;

U.S. Patent Publication Nos. 2007/0156088; 2008/0009789; 2008/0249477 and 2010/0137810; and International Publication Nos. WO2008/029280 and WO2009/040601.

SUMMARY OF THE INVENTION

The present invention seeks to provide an improved injector.

There is thus provided in accordance with a preferred embodiment of the present invention an injector including a syringe arranged along a longitudinal axis, a removable cover for removable engagement with the syringe and a cover removal assembly including an outer portion which is engagable by a user and is movable axially in a cover disengagement direction along an axial travel path with respect to the longitudinal axis and an inner portion which includes at least one engagement portion which is engagable with the removable cover, whereby axial movement of the inner portion in the cover disengagement direction removes the removable cover from the syringe, at least one of the outer portion and the inner portion being configured such as to provide an axially floating lost motion engagement between the outer portion and the inner portion, whereby axial movement of the outer portion in the cover disengagement direction produces corresponding axial movement of the inner portion in the cover disengagement direction along at least a portion of the axial travel path, the length of the portion of the axial travel being a function of the relative axial positioning of the removable cover and the syringe.

There is also provided in accordance with a preferred embodiment of the present invention an injector including a syringe arranged along a longitudinal axis, a removable cover for removable engagement with the syringe and a cover removal assembly including an outer portion which is engagable by a user and is movable axially in a cover disengagement direction along an axial travel path with respect to the longitudinal axis and an inner portion which includes at least one engagement portion which is engagable with the removable cover, whereby axial movement of the inner portion in the cover disengagement direction removes the removable cover from the syringe, the inner portion being configured such as to limit the position of the at least one engagement portion relative to the removable cover in a direction opposite to the cover disengagement direction upon mutual engagement of the inner portion and the removable cover.

In accordance with a preferred embodiment of the present invention at least one of the outer portion and the inner portion is configured such as to provide an axially floating lost motion engagement between the outer portion and the inner portion thereby to take into account variations in the relative axial positioning of the removable cover and the syringe and/or relative in the axial positioning of the cover and the syringe with respect to one or more other parts of the injector such as the housing, whereby axial movement of the outer portion in the cover disengagement direction produces corresponding axial movement of the inner portion in the cover disengagement direction along at least a portion of the axial travel path, the length of the portion of the axial travel path being a function of the relative axial positioning of the cover and the syringe.

It is an additional feature of an embodiment of the present invention that the axially floating motion may be advantageous in cases where the device is accidentally dropped on the outer portion. The above-described axially floating motion engagement between the outer portion and the inner portion may prevent transmission of the resulting impact to the syringe and therefore preserve its integrity.

Preferably, the at least one engagement portion is positionable between the removable cover and a portion of the syringe lying rearwardly thereof.

In accordance with a preferred embodiment of the present invention the axially floating lost motion engagement between the outer portion and the inner portion accommodates variations in the relative axial positioning of the cover and the syringe. Preferably, the axially floating lost motion engagement between the outer portion and the inner portion accommodates manufacturing tolerances and variations in the relative axial positioning of multiple parts of the injector.

Preferably, the inner portion is configured such as to limit the position of the at least one engagement portion relative to the removable cover in a direction opposite to the cover disengagement direction upon mutual engagement of the inner portion and the removable cover.

There is further provided in accordance with yet another preferred embodiment of the present invention an injector including a syringe arranged along a longitudinal axis, a removable cover for removable engagement with the syringe and a cover remover which includes at least one engagement portion which is engagable with the removable cover, whereby axial movement of the cover remover in a cover disengagement direction removes the removable cover from the syringe, the cover remover being configured such as to limit the position of the at least one engagement portion relative to the removable cover in a direction opposite to the cover disengagement direction upon mutual engagement of the cover remover and the removable cover. This structure may be advantageous, for example, in cases where the cover remover is made from plastic material and creep of the at least one engagement portion may otherwise occur during storage of the device, thus possibly reducing the reliability of removal of the removable cover.

Preferably, the syringe includes a needle fixedly mounted therein. Additionally, the removable cover includes a removable needle cover covering the needle. Preferably, the removable needle cover includes a relatively rigid outer portion and a relatively resilient inner portion.

BRIEF DESCRIPTION OF THE DRAWINGS

The present invention will be more fully appreciated from the following detailed description, taken in conjunction with the drawings in which:

FIG. 1 is a simplified exploded view illustration of an injector constructed and operative in accordance with a preferred embodiment of the present invention;

FIGS. 3A, 3B, 3C & 3D are, respectively, a simplified pictorial illustration of an inner portion of a cover removal assembly forming part of the injector of FIGS. 1-2C, a simplified top view of the inner portion, a simplified side view of the inner portion and a simplified sectional illustration taken along lines IIID-IIID in FIG. 3C;

FIGS. 4A, 4B, 4C & 4D are, respectively, a simplified pictorial illustration of an outer portion of a cover removal assembly forming part of the injector of FIGS. 1-2C, a simplified side view of the outer portion, a simplified end view of the outer portion and a simplified sectional illustration taken along lines IVD-IVD in FIG. 4B;

FIG. 4E is a simplified partially cut away pictorial illustration of the outer portion shown in FIGS. 4A-4D;

FIGS. 5A & 5B are, respectively, a simplified side view pictorial illustration of the injector of FIGS. 1-2C and a simplified sectional illustration, taken along lines VB-VB in FIG. 5A, of the inner and outer portions of the cover removal assembly, assembled in the injector in a typical pre-use operative orientation;

FIGS. 6A-6D are simplified sectional illustrations of the inner and outer portions of the cover removal assembly assembled in the injector, in four stages of cover removal for a shortest syringe length and a typically rearwardmost cover position;

FIGS. 8A-8D are simplified sectional illustrations of the inner and outer portions of the cover removal assembly assembled in the injector, in four stages of cover removal for a shortest syringe length and a typically forwardmost cover position;

FIGS. 10A, 10B & 10C are, respectively, top and side view simplified illustrations of the injector of FIG. 9 following complete cover disengagement from the injector and a simplified sectional illustration of the injector of FIGS. 9-10B, taken along lines XC-XC in FIG. 10B.

DETAILED DESCRIPTION OF A PREFERRED EMBODIMENT

Figure 2A:
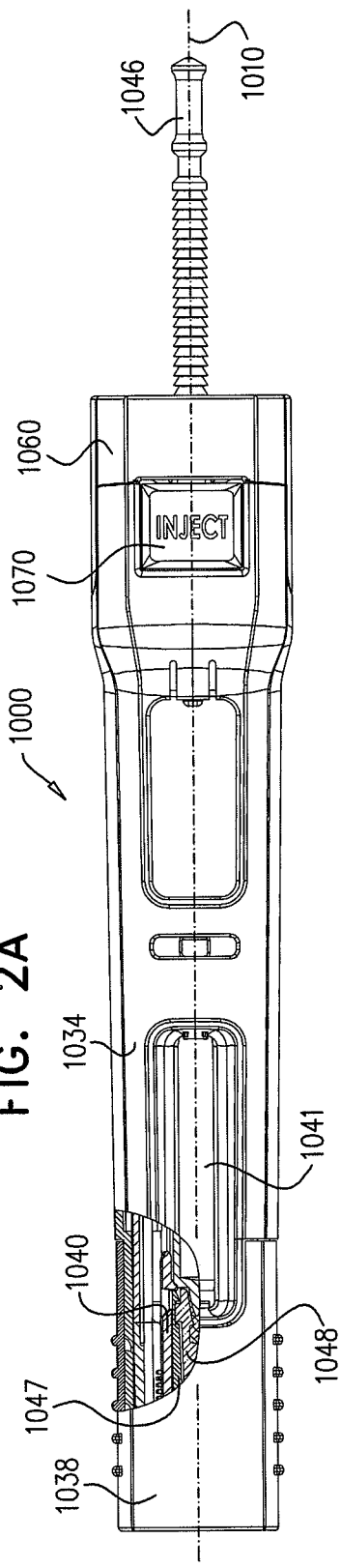
FIGS. 2A and 2B are respective top and side view simplified assembled view illustrations of the injector of FIG. 1 in a pre-use operative orientation.
Figure 2B:
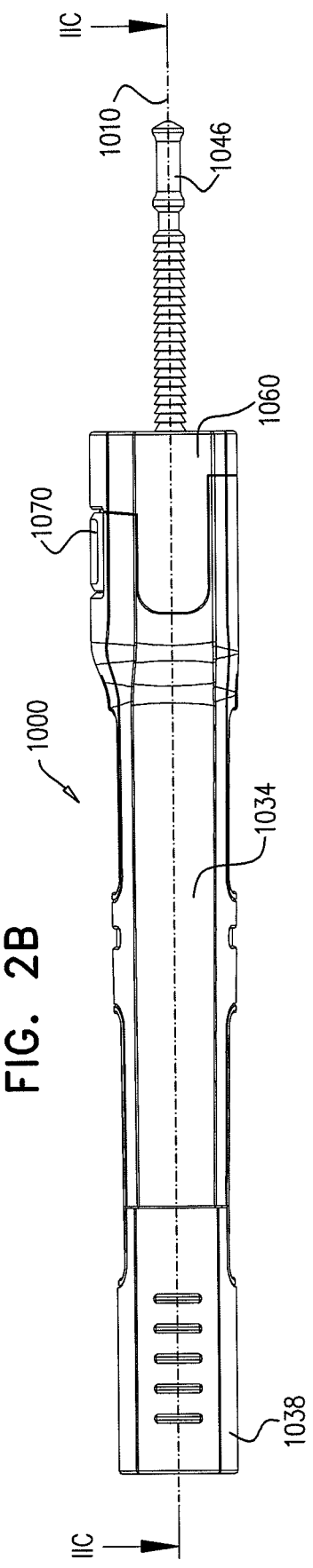
Figure 2C:
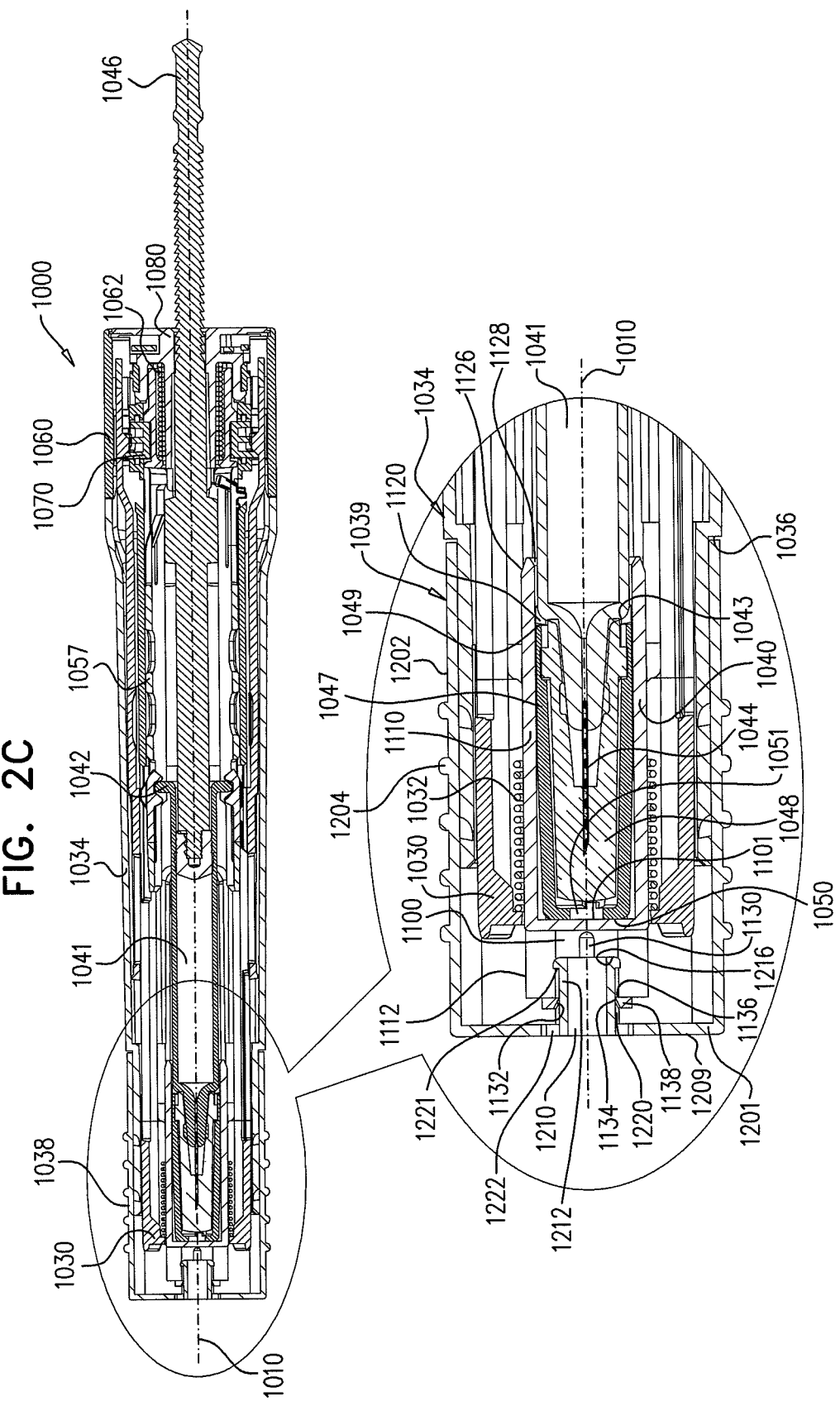
FIG. 2C is a simplified sectional illustration of the injector of FIGS. 2A & 2B, taken along lines IIC-IIC in FIG. 2B.

Reference is now made to FIG. 1, which is a simplified exploded view illustration of an injector 1000 constructed and operative in accordance with a preferred embodiment of the present invention, to FIGS. 2A and 2B, which are respective top and side view simplified assembled view illustrations of the injector of FIG. 1 in a pre-use operative orientation, and to FIG. 2C, which is a simplified sectional illustration of the injector of FIGS. 2A & 2B, taken along lines IIC-IIC in FIG. 2B. Injector 1000 extends generally along an axis 1010.

The injector 1000 comprises a needle guard element 1030, which is positioned by a compression spring 1032 within a forward end of a forward housing 1034, having a forward edge 1036. The forward housing 1034 is operative to engage, at a front end thereof, a cover removal assembly 1038, including an outer portion 1039 and an inner portion 1040.

A syringe 1041, including a rear flange 1042 and a forward-facing surface 1043 and having a hypodermic needle 1044 fixedly mounted therein, which needle is covered by a removable needle cover 1045, such as a rigid needle shield (RNS), is operatively engaged by a plunger 1046 arranged for axial motion along axis 1010. The removable needle cover 1045 preferably includes a relatively rigid outer portion 1047 and a relatively resilient inner portion 1048. Relatively rigid outer portion 1047 is formed with a circumferential rearward facing edge 1049 and a forward surface 1050 having an aperture 1051. Syringe 1041 and plunger 1046 are preferably located within the forward housing 1034. Syringe 1041 may be a conventional syringe, such as a commercially available syringe sold under the catalog designation BD-Hypak™ or may be any other suitable syringe or cartridge. It is appreciated that the length of conventional syringes typically varies within manufacturing tolerances of +/−0.5 mm. It is also appreciated that the axial position of the removable needle cover 1045 relative to the rear flange 1042 typically varies within manufacturing tolerances of +/−1.3 mm. Various other manufacturing tolerances, which may affect the axial position of the removable needle cover 1045 relative to the forward housing 1034, may accumulate to a total of +/−1.1 mm. It is appreciated that the above-referenced tolerances are merely exemplary inasmuch as other syringes may have different tolerances.

Plunger 1046 selectably engages a selectable driving assembly 1057, which includes a selectable driving element 1058 and a pair of elastomeric motion damping elements 1059. Selectable driving assembly 1057 is preferably at least partially seated within a rear housing 1060, forward of a main compression spring 1062, also seated within rear housing 1060. The main compression spring 1062 provides selectable forward axial displacement to the selectable driving assembly 1057. Selectable operation of plunger 1046 by selectable driving assembly 1057 causes the plunger 1046 to inject liquid contents of syringe 1041 through hypodermic needle 1044.

The rear housing 1060 has associated therewith an actuation button 1070, operative to selectably actuate operation of selectable driving assembly 1057. Within rear housing 1060 are seated a rear end element 1080, operative to seal the rear end of the rear housing 1060, and a plunger locking element 1090, cooperative with rear end element 1080 and operative to lock the plunger 1046 when liquid contents of the syringe 1041 should not be injected through needle 1044.

Reference is now made to FIGS. 3A, 3B, 3C & 3D, which are, respectively, a simplified pictorial illustration of an inner portion of a cover removal assembly forming part of the injector of FIGS. 1-2C, a simplified top view of the inner portion, a simplified side view of the inner portion and a simplified sectional illustration taken along lines IIID-IIID in FIG. 3C.

The inner portion 1040 preferably is formed as a unitary, one piece injection molded element and includes a generally circular cylindrical base portion 1100 having a rearward-facing surface 1101. Alternatively, inner portion 1040 can be assembled from multiple parts. From respective oppositely facing locations 1102 and 1104 on an outer surface 1106 thereof extend a pair of mutually facing identical flexible arms 1110. Arms 1110 extend generally axially parallel to a longitudinal axis 1111.

Each arm 1110 includes a pair of mutually spaced axial base portions 1112 which extend outwardly and axially from base portion 1100, a main arm portion 1114, a narrowed portion 1116 and an end portion 1118. Each end portion 1118 preferably includes an engagement portion, preferably in the form of a pair of inner facing teeth 1120, each having a tapered rearward facing surface 1122 and an oppositely tapered forward facing surface 1124. Facing each of surfaces 1124 is a corresponding inwardly tapered rearward-facing end surface 1125 of main arm portion 1114 on each side of narrowed portion 1116. Each end portion 1118 also includes respectively inwardly and outwardly tapered outer and inner rearward-facing ends 1126 and 1128.

The base portion 1100 preferably includes a pair of axial slots 1130 which extend forwardly from an axially rearward end thereof intermediate arms 1110.

A pair of inwardly facing teeth 1132 are disposed inwardly and rearwardly of cylindrical base portion 1100 intermediate each pair of axial base portions 1112. Each of teeth 1132 has a forwardly tapered radially inwardly and forwardly facing surface 1134 and a rearwardly facing surface 1136 which is generally perpendicular to axis 1111. Teeth 1132 are each preferably supported on a bridge portion 1138 which lies outwardly and forwardly of cylindrical base portion 1110, forwardly bridging each pair of axial base portions 1112.

Reference is now made to FIGS. 4A, 4B, 4C & 4D, which are, respectively, a simplified pictorial illustration of outer portion 1039 of cover removal assembly 1038 forming part of the injector 1000 of FIGS. 1-2C, a simplified side view of outer portion 1039, a simplified end view of outer portion 1039 and a simplified sectional illustration taken along lines IVD-IVD in FIG. 4B, and to FIG. 4E, which is a simplified partially cut away pictorial illustration of the outer portion shown in FIGS. 4A-4D.

As seen in FIGS. 4A-4E, the outer portion 1039 is in the form of a generally cylindrical cap having a generally cylindrical overall shape with a partially flattened circular cross-section perpendicular to an axis 1200. As seen in FIGS. 4A-4E, outer portion 1039 includes a base 1201, a pair of edge surfaces 1202, each having an array of grip-enhancing protrusions 1204, and a pair of side surfaces 1206, each having a rearward-facing, generally square, cut out 1208 formed therein. Base 1201 has a forward facing surface 1209.

Base 1201 is preferably formed with a central aperture 1210 which communicates with the interior of a generally circular cylindrical rearward-facing tubular portion 1212. Tubular portion 1212 has a tapered rearward-facing end surface 1216 and includes a pair of mutually circumferentially spaced axially-extending protrusions 1218 as well as a pair of mutually circumferentially spaced, axially-extending recesses 1220, generally evenly spaced between protrusions 1218. Recesses 1220 each include a forward facing circumferential surface 1221 which is generally perpendicular to axis 1200.

Base 1201 is formed with a pair of arcuate apertures 1222 each of which communicates with a corresponding recess 1220 and with the interior of outer portion 1039 outside tubular portion 1212.

Needle guard element 1030 is preferably identical to that shown in FIGS. 65-67B of Published PCT Patent Application WO 2008/047372 and described therein. The disclosure of Published PCT Patent Application WO 2008/047372 is hereby incorporated by reference.

As described in detail in Published PCT Patent Application WO 2008/047372, needle guard element 1030 includes a pair of restriction elements, which prevent actuation of the device when a user presses actuation button 1070 when the device is not pressed against the user's body. At a forward part of the needle guard element 1030 there is provided a cylindrical portion having a front end including a generally circular bore, through which the needle passes during injection of the drug. Following injection, the cylindrical portion is displaced forwardly relative to the needle, thereby covering the needle and preventing inadvertent needle pricks.

Forward housing 1034 is preferably identical to that shown in FIGS. 68-70C of Published PCT Patent Application WO 2008/047372 and described therein. The disclosure of Published PCT Patent Application WO 2008/047372 is hereby incorporated by reference.

As described in detail in Published PCT Patent Application WO 2008/047372, the forward housing 1034 includes at a rear end thereof a cutout portion 1402 adapted to accommodate the actuation button 1070.

As seen in FIG. 1, plunger 1046 includes a threaded protrusion 1470, which threadably engages a corresponding threaded socket (not shown) formed in a rear surface of the piston of syringe 1043. Rearwardly of threaded protrusion 1470 is a generally circular cylindrical portion 1472 having a first cross sectional radius, followed by a relatively short circular cylindrical portion 1474 having a second cross sectional radius greater than the first radius and defining a rearward facing shoulder 1475.

Rearward of portion 1474 is a third generally circular cylindrical portion 1476 having a third cross sectional radius, generally equal to the first radius. Rearwardly of portion 1476 is formed a toothed portion 1477, each tooth thereof having a generally transverse forwardly facing portion and a slanted rearwardly facing portion. The particular shape of the teeth of toothed portion 1477 enables rearward movement of the plunger 1046 at any time, and requires a specific configuration of the device in order to enable forward movement of the plunger 1046.

Plunger 1046 is preferably symmetrically disposed about a longitudinal axis.

Selectable driving assembly 1057 is preferably identical to that shown in FIGS. 71-73B of Published PCT Patent Application WO 2008/047372 and described therein. The disclosure of Published PCT Patent Application WO 2008/047372 is hereby incorporated by reference.

As described in detail in Published PCT Patent Application WO 2008/047372, the selectable driving assembly 1057 includes selectable driving element 1058 and elastomeric motion damping elements 1059. Selectable driving element 1058 includes a rearward facing generally cylindrical portion and a pair of longitudinal arms. At a forward end of each of the longitudinal arms there is provided a first hinged finger, having formed thereon a pair of inwardly facing protrusions. The inwardly facing protrusions are adapted to engage the flange 1042 of syringe 1041 to retain it in position prior to actuation of the injector and to control its forward movement during actuation thereof.

Rearwardly of the first hinged finger on each of longitudinal arms is a second hinged finger, having an inwardly facing protrusion, which is adapted to rearwardly displace the syringe 1041 following injection, when the needle guard element 1030 is rearwardly displaced.

Generally alongside and parallel to second hinged fingers there are formed third hinged fingers, each including an inwardly facing slanted protrusion operative to forwardly displace the plunger 1046 during injection, and a pair of outwardly facing protrusions, which are operative to inwardly bend the third hinged fingers during actuation and which engage the needle guard element 1030 and are operative to displace it forwardly as soon as the injector disengages the user's body.

A cylindrical portion of the selectable driving assembly 1057 includes protrusions on opposite sides thereof, which are adapted to maintain the selectable driving assembly 1057 in place when the injector is in its storage position, by abutting against the actuation button 1070. The cylindrical portion also has seated therein motion damping elements 1059 which engage an internal surface of the rear housing 1060, and thus are operative to slow the forward movement of the selectable driving assembly 1057, thereby slowing the forward movement of the syringe 1041 and plunger 1046 during injection.

Rear housing 1060 is preferably identical to that shown in FIGS. 74-76C of Published PCT Patent Application WO 2008/047372 and described therein. The disclosure of Published PCT Patent Application WO 2008/047372 is hereby incorporated by reference.

As described in detail in Published PCT Patent Application WO 2008/047372, the rear housing 1060 preferably is an integrally formed element, preferably injection molded of plastic and preferably has a generally cylindrical configuration arranged about a longitudinal axis. The rear housing 1060 includes a tube, which includes a forward portion having an interiorly facing surface including four generally equally spaced, longitudinally extending, guiding ribs. Also formed on the interiorly facing surface are a pair of interiorly facing protrusions whose width tapers in a forwardly facing direction to a point, thus defining a generally triangular engagement surface for elastomeric motion damping elements 1059. Disposed adjacent the wide end of each of the protrusions are an inclined recess and a cylindrical recess, which serve to guide elastomeric damping elements 1059 upstream of their engagement with the protrusions.

Formed on a pair of generally equally spaced exteriorly facing surfaces of the tube are respective generally rectangular outwardly protruding frames. Further protrusions are located interiorly of the respective frames and are centered adjacent rearward ends thereof. These protrusions are accommodated in snap fit engagement sockets of the forward housing 1034 during factory assembly of the device, and thereby maintain the connection between the rear housing 1060 and the forward housing 1034. Formed in the tube adjacent a rearward end thereof are a pair of side cutouts each having an undercut forward edge. Disposed forwardly of each of edges is a generally rectangular outwardly facing protrusion.

Actuation button 1070 is preferably identical to that shown in FIGS. 77A-79B of Published PCT Patent Application WO 2008/047372 and described therein. The disclosure of Published PCT Patent Application WO 2008/047372 is hereby incorporated by reference.

Rear end element 1080 is preferably identical to that shown in FIGS. 83-85C of Published PCT Patent Application WO 2008/047372 and described therein. The disclosure of Published PCT Patent Application WO 2008/047372 is hereby incorporated by reference.

Plunger locking element 1090 is preferably identical to that shown in FIGS. 80-82B of Published PCT Patent Application WO 2008/047372 and described therein. The disclosure of Published PCT Patent Application WO 2008/047372 is hereby incorporated by reference.

Various further stages of typical use of the injector of FIGS. 1-2C are illustrated in FIGS. 86E-86L of Published PCT Patent Application WO 2008/047372 and described therein. The disclosure of Published PCT Patent Application WO 2008/047372 is hereby incorporated by reference.

Reference is now made to FIGS. 5A and 5B, which are, respectively, a simplified side view pictorial illustration of the injector of FIGS. 1-2C and a simplified sectional illustration of the inner and outer portions of the cover removal assembly, assembled in the injector in a typical pre-use operative orientation with respect to syringe 1041, needle 1044 and removable needle cover 1045. It is a particular feature of the present invention that the structure which will now be described in detail with reference to FIG. 5B produces reliable removal of needle cover 1045 notwithstanding the above-described cumulative manufacturing tolerances relating to the various portions of the injector.

The illustration of FIG. 5B shows the syringe 1041 having a length along axis 1111, which is within its manufacturing tolerances as described hereinabove but not at either extreme thereof. Similarly, the illustration of FIG. 5B shows axial placement of the removable needle cover 1045 along axis 1111 at a location relative to the syringe 1041 which is within its manufacturing tolerances as described hereinabove but not at either extreme thereof.

As seen in FIG. 5B, when the injector is in a typical pre-use operative orientation, forward-facing surface 1043 is positioned along axis 1111 forwardly of and at a typical separation of 7.5 mm from forward edge 1036 of forward housing 1034. Rearward facing edge 1049 of relatively rigid outer portion 1047 of removable needle cover 1045 is positioned along axis 1111 forwardly of and at a typical separation of 8.8 mm from forward edge 1036 of forward housing 1034.

Rearward facing surface 1101 of inner portion 1040 lies up against forward facing surface 1050 of the relatively rigid outer portion 1047 of removable needle cover 1045 and is positioned along axis 1111 rearwardly of and at a typical separation of 9.4 mm from forward-facing surface 1209 of base 1201 of outer portion 1039. Forward-facing surface 1209 of base 1201 of outer portion 1039 is positioned along axis 1111 forwardly of and at a typical separation of 44.6 mm from forward edge 1036 of forward housing 1034.

Cylindrical base portion 1100 of inner portion 1040 partially overlies generally circular cylindrical rearward-facing tubular portion 1212 of outer portion 1039, in axially sliding relationship therewith, with protrusions 1218 (not shown) of outer portion 1039 lying in axial slidable engagement with corresponding axial slots 1130 of inner portion 1040. Teeth 1132 of inner portion 1040 lie in axial slidable engagement with corresponding recesses 1220 of outer portion 1039.

It is seen that teeth 1120 of inner portion 1040 lie immediately behind and in engagement with rearward facing edge 1049 of removable needle cover 1045. It is also seen that forward facing circumferential surface 1221 of outer portion 1039 lies rearwardly of and is spaced from rearwardly facing surfaces 1136 of teeth 1132 of inner portion 1040.

Reference is now made to FIGS. 6A-6D, which are simplified sectional illustrations of the inner and outer portions of the cover removal assembly assembled in the injector, in four stages of cover removal for a shortest syringe length and a typically rearwardmost cover position.

FIG. 6A shows the syringe 1041 having a length along axis 1111, which is the shortest possible length which is within its manufacturing tolerances as described hereinabove. Similarly, FIG. 6A shows axial placement of the removable needle cover 1045 along axis 1111 at the rearwardmost location relative to the syringe 1041 which is within its manufacturing tolerances as described hereinabove.

As seen in FIG. 6A, when the injector is in a typical pre-use operative orientation, forward-facing surface 1043 is positioned along axis 1111 forwardly of and at a typical separation of 4.8 mm from forward edge 1036 of forward housing 1034. Rearward facing edge 1049 of relatively rigid outer portion 1047 of removable needle cover 1045 is positioned along axis 1111 forwardly of and at a typical separation of 5.4 mm from forward edge 1036 of forward housing 1034.

Rearward facing surface 1101 of inner portion 1040 lies up against forward facing surface 1050 of the relatively rigid outer portion 1047 of removable needle cover 1045 and is positioned along axis 1111 rearwardly of and at a typical separation of 12.8 mm from forward-facing surface 1209 of base 1201 of outer portion 1039. Forward-facing surface 1209 of base 1201 of outer portion 1039 is positioned along axis 1111 forwardly of and at a typical separation of 44.6 mm from forward edge 1036 of forward housing 1034.

Cylindrical base portion 1100 of inner portion 1040 partially overlies generally circular cylindrical rearward-facing tubular portion 1212 of outer portion 1039, in axially sliding relationship therewith, with protrusions 1218 (not shown) of outer portion 1039 lying in axial slidable engagement with corresponding axial slots 1130 of inner portion 1040. Teeth 1132 of inner portion 1040 lie in axial slidable engagement with corresponding recesses 1220 of outer portion 1039.

It is seen that forward facing circumferential surface 1221 lies rearwardly of and in touching engagement with rearwardly facing surfaces 1136 of teeth 1132 of inner portion 1040.

Turning now to FIG. 6B, it is seen that cover removal assembly 1038 is moved forwardly with respect to the forward housing 1034, to the left in the sense of FIGS. 6A-6D, such that forward-facing surface 1209 of base 1201 of outer portion 1039 is positioned along axis 1111 at a typical separation of 47 mm from forward edge 1036 of forward housing 1034. The axial separation between forward-facing surface 1043 and forward edge 1036 of forward housing 1034 remains at a typical separation of 4.8 mm.

In this case, due to the extremely short length of the syringe and the rearwardmost cover position, there is no axially floating lost motion engagement between outer portion 1039 and inner portion 1040, as rearwardly facing surfaces 1136 of teeth 1132 of inner portion 1040 are engaged by and pulled forward by forward facing circumferential surface 1221 of outer portion 1039 causing a corresponding movement of the inner portion 1040 with the removable needle cover 1045 therewithin and thus the axial separation along axis 1111 of rearward facing edge 1049 of relatively rigid outer portion 1047 of removable needle cover 1045 from forward edge 1036 of forward housing 1034 increases to 7.8 mm.

The axial separation between rearward facing surface 1101 of inner portion 1040 and forward-facing surface 1209 of base 1201 of outer portion 1039 remains 12.8 mm.

Turning now to FIG. 6C, it is seen that cover removal assembly 1038 is moved further forwardly with respect to the forward housing 1034, to the left in the sense of FIGS. 6A-6D, such that forward-facing surface 1209 of base 1201 of outer portion 1039 is positioned along axis 1111 at a typical separation of 49.4 mm from forward edge 1036 of forward housing 1034.

In this case, due to the extremely short length of the syringe and the rearwardmost cover position, there is no axially floating lost motion engagement between outer portion 1039 and inner portion 1040 and thus the axial separation along axis 1111 of rearward facing edge 1049 of relatively rigid outer portion 1047 of removable needle cover 1045 from forward edge 1036 of forward housing 1034 increases to 10.2 mm.

The axial separation between rearward facing surface 1101 of inner portion 1040 and forward-facing surface 1209 of base 1201 of outer portion 1039 remains 12.8 mm.

Turning now to FIG. 6D, it is seen that cover removal assembly 1038 is moved further forwardly with respect to the forward housing 1034, to the left in the sense of FIGS. 6A-6D, such that forward-facing surface 1209 of base 1201 of outer portion 1039 is positioned along axis 1111 at a typical separation of 53 mm from forward edge 1036 of forward housing 1034.

There is no axially floating lost motion engagement between outer portion 1039 and inner portion 1040 and thus the axial separation along axis 1111 of rearward facing edge 1049 of relatively rigid outer portion 1047 of removable needle cover 1045 from forward edge 1036 of forward housing 1034 increases to 13.8 mm.

The axial separation between rearward facing surface 1101 of inner portion 1040 and forward-facing surface 1209 of base 1201 of outer portion 1039 remains 12.8 mm.

Reference is now made to FIGS. 7A-7D, which are simplified sectional illustrations of the inner and outer portions of the cover removal assembly assembled in the injector, in four stages of cover removal for a longest syringe length and a typically rearwardmost cover position.

Figure 7A:
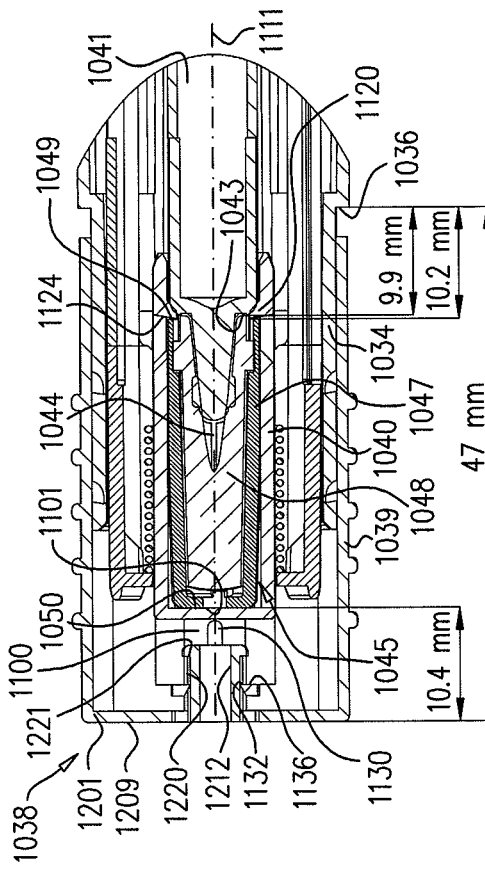
FIGS. 7A-7D are simplified sectional illustrations of the inner and outer portions of the cover removal assembly assembled in the injector, in four stages of cover removal for a longest syringe length and a typically rearwardmost cover position.

FIG. 7A shows the syringe 1041 having a length along axis 1111, which is the longest possible length which is within its manufacturing tolerances as described hereinabove. Similarly, FIG. 7A shows axial placement of the removable needle cover 1045 along axis 1111 at the rearwardmost location relative to the syringe 1041 which is within its manufacturing tolerances as described hereinabove.

As seen in FIG. 7A, when the injector is in a typical pre-use operative orientation, forward-facing surface 1043 is positioned along axis 1111 forwardly of and at a typical separation of 9.9 mm from forward edge 1036 of forward housing 1034. Rearward facing edge 1049 of relatively rigid outer portion 1047 of removable needle cover 1045 is positioned along axis 1111 forwardly of and at a typical separation of 10.2 mm from forward edge 1036 of forward housing 1034.

Rearward facing surface 1101 of inner portion 1040 lies up against forward facing surface 1050 of the relatively rigid outer portion 1047 of removable needle cover 1045 and is positioned along axis 1111 rearwardly of and at a typical separation of 8 mm from forward-facing surface 1209 of base 1201 of outer portion 1039. Forward-facing surface 1209 of base 1201 of outer portion 1039 is positioned along axis 1111 forwardly of and at a typical separation of 44.6 mm from forward edge 1036 of forward housing 1034.

Cylindrical base portion 1100 of inner portion 1040 partially overlies generally circular cylindrical rearward-facing tubular portion 1212 of outer portion 1039, in axially sliding relationship therewith, with protrusions 1218 (not shown) of outer portion 1039 lying in axial slidable engagement with corresponding axial slots 1130 of inner portion 1040. Teeth 1132 of inner portion 1040 lie in axial slidable engagement with corresponding recesses 1220 of outer portion 1039. It is seen that forward facing circumferential surface 1221 of outer portion 1039 lies rearwardly and spaced from rearwardly facing surfaces 1136 of teeth 1132 of inner portion 1040.

Figure 7B:
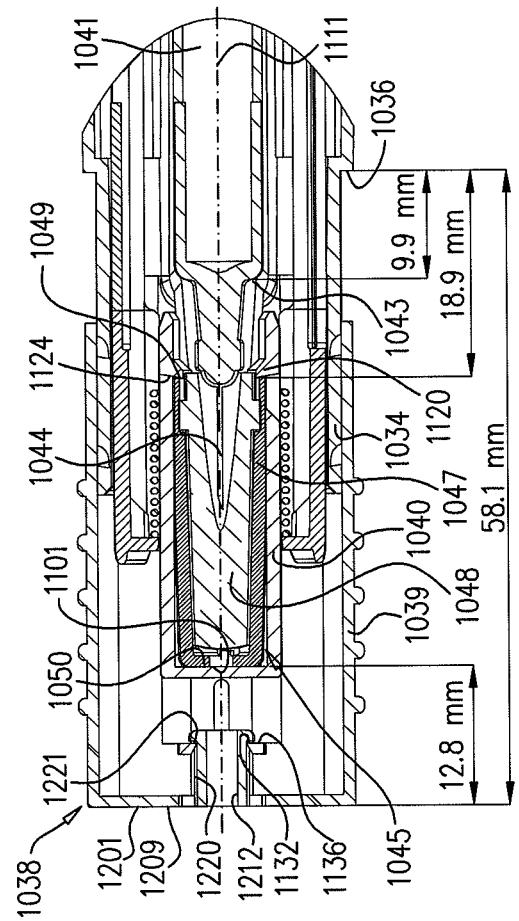

Turning now to FIG. 7B, it is seen that cover removal assembly 1038 is moved forwardly with respect to the forward housing 1034, to the left in the sense of FIGS. 7A-7D, such that forward-facing surface 1209 of base 1201 of outer portion 1039 is positioned along axis 1111 at a typical separation of 47 mm from forward edge 1036 of forward housing 1034. The axial separation between forward-facing surface 1043 and forward edge 1036 of forward housing 1034 remains at a typical separation of 9.9 mm.

Due to the axially floating lost motion engagement between outer portion 1039 and inner portion 1040, this forward motion does not change the axial separation along axis 1111 between rearward facing edge 1049 of relatively rigid outer portion 1047 of removable needle cover 1045 and forward edge 1036 of forward housing 1034, which remains at a typical separation of 10.2 mm.

The axial separation between rearward facing surface 1101 of inner portion 1040 and forward-facing surface 1209 of base 1201 of outer portion 1039 increases to 10.4 mm.

Figure 7C:
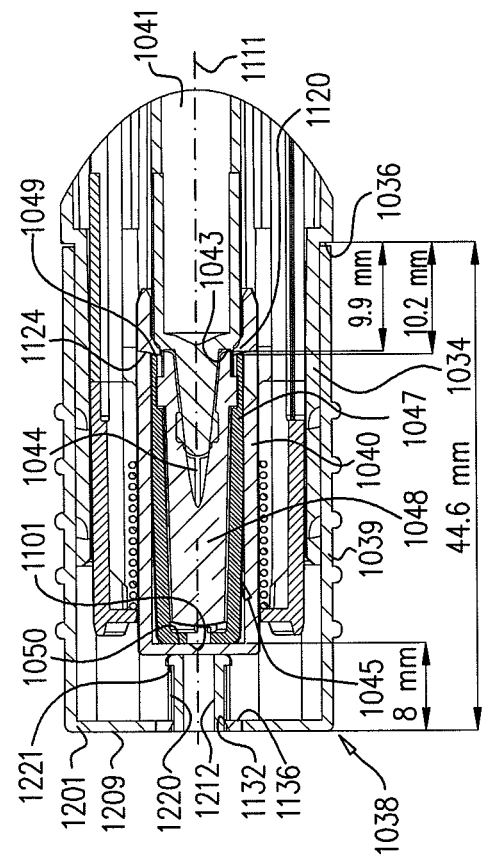

Turning now to FIG. 7C, it is seen that cover removal assembly 1038 is moved further forwardly with respect to the forward housing 1034, to the left in the sense of FIGS. 7A-7D, such that forward-facing surface 1209 of base 1201 of outer portion 1039 is positioned along axis 1111 at a typical separation of 49.4 mm from forward edge 1036 of forward housing 1034.

Due to the axially floating lost motion engagement between outer portion 1039 and inner portion 1040, this forward motion does not change the axial separation along axis 1111 between rearward facing edge 1049 of relatively rigid outer portion 1047 of removable needle cover 1045 and forward edge 1036 of forward housing 1034, which remains at a typical separation of 10.2 mm. It is seen that forward facing circumferential surface 1221 lies rearwardly of and in touching engagement with rearwardly facing surfaces 1136 of teeth 1132 of inner portion 1040.

The axial separation between rearward facing surface 1101 of inner portion 1040 and forward-facing surface 1209 of base 1201 of outer portion 1039 increases to 12.8 mm.

Figure 7D:
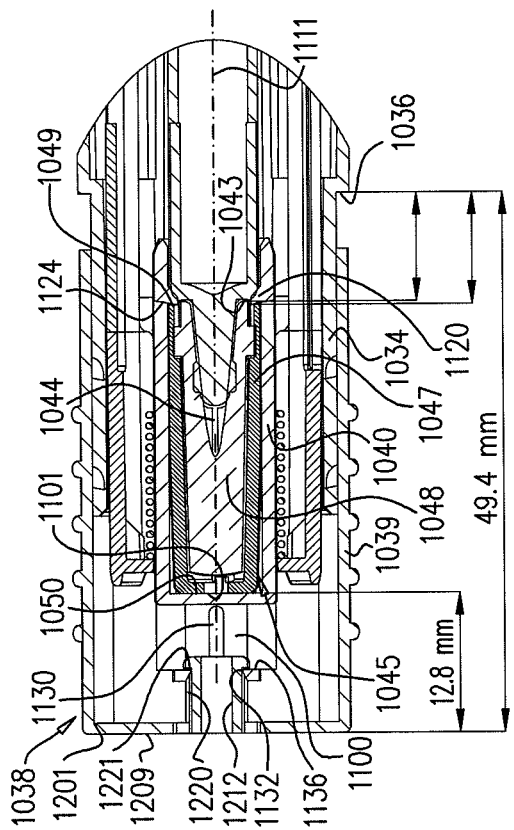

Turning now to FIG. 7D, it is seen that cover removal assembly 1038 is moved further forwardly with respect to the forward housing 1034, to the left in the sense of FIGS. 7A-7D, such that forward-facing surface 1209 of base 1201 of outer portion 1039 is positioned along axis 1111 at a typical separation of 58.1 mm from forward edge 1036 of forward housing 1034.

At this stage there is no remaining available axially floating lost motion between outer portion 1039 and inner portion 1040 as rearwardly facing surfaces 1136 of teeth 1132 of inner portion 1040 are engaged by and pulled forward by forward facing circumferential surface 1221 of outer portion 1039 causing a corresponding movement of the inner portion 1040 with the removable needle cover 1045 therewithin and thus the axial separation along axis 1111 of rearward facing edge 1049 of relatively rigid outer portion 1047 of removable needle cover 1045 from forward edge 1036 of forward housing 1034 increases to 18.9 mm.

The axial separation between rearward facing surface 1101 of inner portion 1040 and forward-facing surface 1209 of base 1201 of outer portion 1039 remains 12.8 mm.

Reference is now made to FIGS. 8A-8D, which are simplified sectional illustrations of the inner and outer portions of the cover removal assembly assembled in the injector in four stages of cover removal for a shortest syringe length and a typically forwardmost cover position.

FIG. 8A shows the syringe 1041 having a length along axis 1111, which is the shortest possible length which is within its manufacturing tolerances as described hereinabove. Similarly, FIG. 8A shows axial placement of the removable needle cover 1045 along axis 1111 at the forwardmost location relative to the syringe 1041 which is within its manufacturing tolerances as described hereinabove.

As seen in FIG. 8A, when the injector is in a typical pre-use operative orientation, forward-facing surface 1043 is positioned along axis 1111 forwardly of and at a typical separation of 4.8 mm from forward edge 1036 of forward housing 1034. Rearward facing edge 1049 of relatively rigid outer portion 1047 of removable needle cover 1045 is positioned along axis 1111 forwardly of and at a typical separation of 10.2 mm from forward edge 1036 of forward housing 1034.

Rearward facing surface 1101 of inner portion 1040 lies up against forward facing surface 1050 of the relatively rigid outer portion 1047 of removable needle cover 1045 and is positioned along axis 1111 rearwardly of and at a typical separation of 8 mm from forward-facing surface 1209 of base 1201 of outer portion 1039. Forward-facing surface 1209 of base 1201 of outer portion 1039 is positioned along axis 1111 forwardly of and at a typical separation of 44.6 mm from forward edge 1036 of forward housing 1034.

Cylindrical base portion 1100 of inner portion 1040 partially overlies generally circular cylindrical rearward-facing tubular portion 1212 of outer portion 1039, in axially sliding relationship therewith, with protrusions 1218 (not shown) of outer portion 1039 lying in axial slidable engagement with corresponding axial slots 1130 of inner portion 1040. Teeth 1132 of inner portion 1040 lie in axial slidable engagement with corresponding recesses 1220 of outer portion 1039. It is seen that forward facing circumferential surface 1221 of outer portion 1039 lies rearwardly and spaced from rearwardly facing surfaces 1136 of teeth 1132 of inner portion 1040.

Turning now to FIG. 8B, it is seen that cover removal assembly 1038 is moved forwardly with respect to the forward housing 1034, to the left in the sense of FIGS. 8A-8D, such that forward-facing surface 1209 of base 1201 of outer portion 1039 is positioned along axis 1111 at a typical separation of 47 mm from forward edge 1036 of forward housing 1034. The axial separation between forward-facing surface 1043 and forward edge 1036 of forward housing 1034 remains at a typical separation of 4.8 mm.

Due to the axially floating lost motion engagement between outer portion 1039 and inner portion 1040, this forward motion does not change the axial separation along axis 1111 between rearward facing edge 1049 of relatively rigid outer portion 1047 of removable needle cover 1045 and forward edge 1036 of forward housing 1034, which remains at a typical separation of 10.2 mm.

The axial separation between rearward facing surface 1101 of inner portion 1040 and forward-facing surface 1209 of base 1201 of outer portion 1039 increases to 10.4 mm.

Turning now to FIG. 8C, it is seen that cover removal assembly 1038 is moved further forwardly with respect to the forward housing 1034, to the left in the sense of FIGS. 8A-8D, such that forward-facing surface 1209 of base 1201 of outer portion 1039 is positioned along axis 1111 at a typical separation of 49.4 mm from forward edge 1036 of forward housing 1034.

Due to the axially floating lost motion engagement between outer portion 1039 and inner portion 1040, this forward motion does not change the axial separation along axis 1111 between rearward facing edge 1049 of relatively rigid outer portion 1047 of removable needle cover 1045 and forward edge 1036 of forward housing 1034, which remains at a typical separation of 10.2 mm. It is seen that forward facing circumferential surface 1221 lies rearwardly of and in touching engagement with rearwardly facing surfaces 1136 of teeth 1132 of inner portion 1040.

The axial separation between rearward facing surface 1101 of inner portion 1040 and forward-facing surface 1209 of base 1201 of outer portion 1039 increases to 12.8 mm.

Turning now to FIG. 8D, it is seen that cover removal assembly 1038 is moved further forwardly with respect to the forward housing 1034, to the left in the sense of FIGS. 8A-8D, such that forward-facing surface 1209 of base 1201 of outer portion 1039 is positioned along axis 1111 at a typical separation of 53 mm from forward edge 1036 of forward housing 1034.

At this stage there is no remaining available axially floating lost motion between outer portion 1039 and inner portion 1040 as rearwardly facing surfaces 1136 of teeth 1132 of inner portion 1040 are engaged by and pulled forward by forward facing circumferential surface 1221 of outer portion 1039 causing a corresponding movement of the inner portion 1040 with the removable needle cover 1045 therewithin and thus the axial separation along axis 1111 of rearward facing edge 1049 of relatively rigid outer portion 1047 of removable needle cover 1045 from forward edge 1036 of forward housing 1034 increases to 13.8 mm.

The axial separation between rearward facing surface 1101 of inner portion 1040 and forward-facing surface 1209 of base 1201 of outer portion 1039 remains 12.8 mm.

Figure 9:
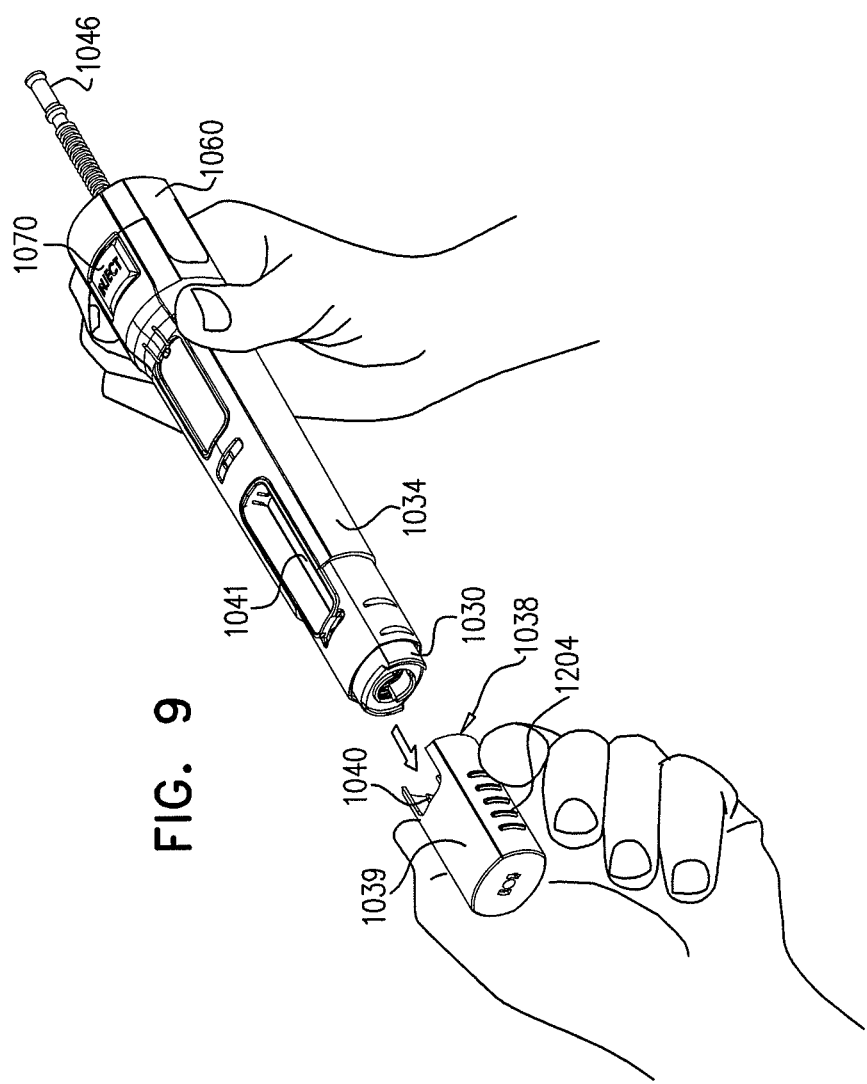
FIG. 9 is a simplified illustration of complete cover disengagement from the injector.
Figure 10A:
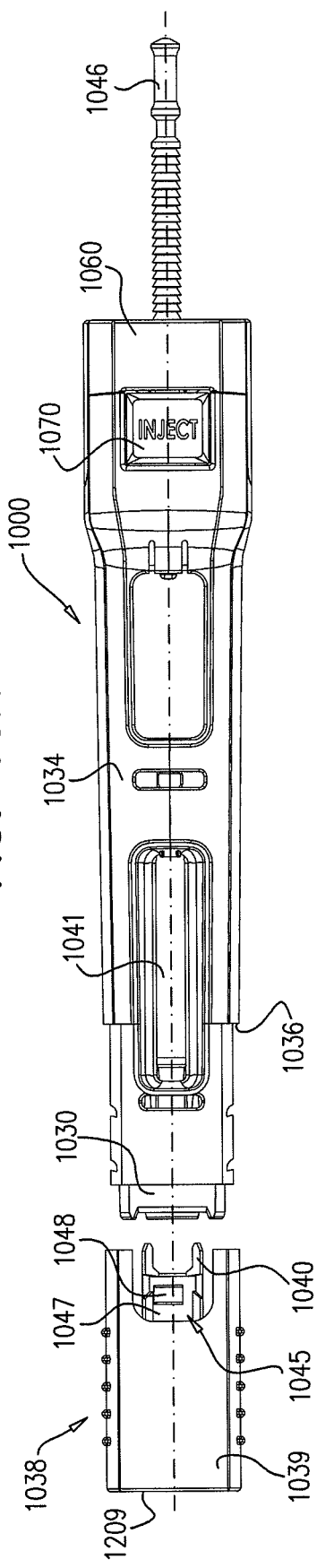
Figure 10B:
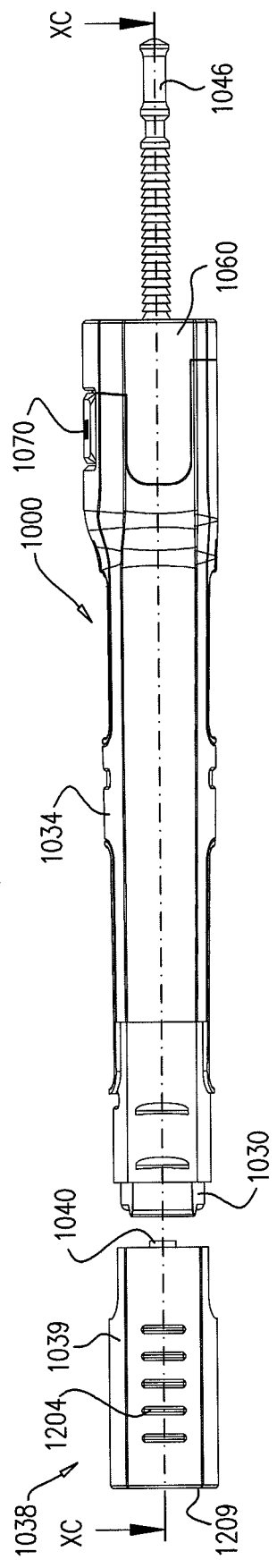

FIGS. 9-10C show complete disengagement of the cover removal assembly 1038 and the removable needle cover 1045 from the reminder of the injector.

It will be appreciated by persons skilled in the art that the present invention is not limited to what has been particularly described hereinabove. Rather the scope of the invention is intended to include both combinations and subcombinations of various features described hereinabove as well as modifications and variations thereof that would occur to persons skilled in the art upon reading the foregoing and which are not in the prior art.

The invention claimed is:

1. An injector comprising:
a syringe arranged along a longitudinal axis and having a forward end and a rearward end;
a removable cover for removable engagement with said forward end of said syringe; and
a cover removal assembly comprising:
an outer portion which is engagable by a user and is movable axially in a cover disengagement direction along an axial travel path with respect to said longitudinal axis; and
an inner portion which includes at least one engagement portion which is engagable with a rearward end of said removable cover, whereby axial movement of said inner portion in said cover disengagement direction removes said removable cover from said syringe,
said outer portion and said inner portion being movable relative to one another in an axial direction along said longitudinal axis during use,
said inner portion also including a rearward facing surface which lies up against a forward surface located at said forward end of said removable cover, which is opposite said rearward end of said removable cover, and wherein said rearward facing surface is configured such that said forward end of said removable cover limits the movement of said rearward facing surface in a direction opposite to said cover disengagement direction, thereby limiting the position of said at least one engagement portion relative to said removable cover in a direction opposite to said cover disengagement direction upon mutual engagement of said inner portion and said removable cover.

2. An injector according to claim 1 and wherein at least one of said outer portion and said inner portion is configured such as to provide an axially floating lost motion engagement between said outer portion and said inner portion thereby to take into account variations in the relative axial positioning of said removable cover and said syringe, whereby axial movement of said outer portion in said cover disengagement direction produces corresponding axial movement of said inner portion in said cover disengagement direction along at least a portion of said axial travel path, the length of said portion of said axial travel path being a function of the relative axial positioning of said removable cover and said syringe.

3. An injector according to claim 2 and wherein said axially floating lost motion engagement between said outer portion and said inner portion accommodates variations in the relative axial positioning of the cover and the syringe.

4. An injector according to claim 2 and wherein said axially floating lost motion engagement between said outer portion and said inner portion accommodates manufacturing tolerances and variations in the relative axial positioning of multiple parts of said injector.

5. An injector according to claim 1 and wherein said at least one engagement portion is positionable between said removable cover and a portion of said syringe lying rearwardly thereof.

6. An injector according to claim 1 and wherein said syringe includes a needle fixedly mounted therein.

7. An injector according to claim 6 and wherein said removable cover comprises a removable needle cover covering said needle.

8. An injector according to claim 7 and wherein said removable needle cover includes a relatively rigid outer portion and a relatively resilient inner portion.

9. The injector according to claim 1, wherein said outer portion and said inner portion are movable relative to one another during removal of said removable cover from said forward end of said syringe.

* * * * *